(12) United States Patent
Srinivasan et al.

(10) Patent No.: US 12,265,184 B2
(45) Date of Patent: Apr. 1, 2025

(54) APPARATUS, SYSTEM AND METHOD TO COMPOUND SIGNALS OF RESPECTIVE RECEIVED ULTRASONIC FREQUENCIES TO GENERATE AN OUTPUT ULTRASONIC IMAGE

(71) Applicant: Exo Imaging, Inc., Redwood City, CA (US)

(72) Inventors: Seshadri Srinivasan, Fremont, CA (US); Ruiying Zhang, San Jose, CA (US)

(73) Assignee: Exo Imaging, Inc., Santa Clara, CA (US)

( * ) Notice: Subject to any disclaimer, the term of this patent is extended or adjusted under 35 U.S.C. 154(b) by 236 days.

(21) Appl. No.: 17/590,947

(22) Filed: Feb. 2, 2022

(65) Prior Publication Data

US 2023/0243944 A1 Aug. 3, 2023

(51) Int. Cl.
| | |
|---|---|
| *G01S 7/52* | (2006.01) |
| *A61B 8/00* | (2006.01) |
| *A61B 8/12* | (2006.01) |
| *G01S 15/89* | (2006.01) |
| *G06V 10/26* | (2022.01) |
| *G06V 10/60* | (2022.01) |
| *G06V 10/774* | (2022.01) |
| *G06V 10/776* | (2022.01) |

(52) U.S. Cl.
CPC ...... *G01S 7/52003* (2013.01); *G01S 15/8977* (2013.01); *G06V 10/26* (2022.01); *G06V 10/60* (2022.01); *G06V 10/774* (2022.01); *G06V 10/776* (2022.01); *A61B 8/12* (2013.01); *A61B 8/4281* (2013.01)

(58) Field of Classification Search
None
See application file for complete search history.

(56) References Cited

U.S. PATENT DOCUMENTS

| | | | | |
|---|---|---|---|---|
| 10,687,788 | B2 * | 6/2020 | Kang | A61B 8/5207 |
| 11,953,591 | B2 * | 4/2024 | Shin | A61B 8/54 |
| 2007/0083114 | A1 * | 4/2007 | Yang | A61B 8/00 |
| | | | | 600/437 |
| 2011/0098565 | A1 * | 4/2011 | Masuzawa | G01S 7/5209 |
| | | | | 600/443 |
| 2012/0232392 | A1 * | 9/2012 | Tanabe | A61B 8/4281 |
| | | | | 600/443 |
| 2013/0012819 | A1 * | 1/2013 | Haugen | G01S 15/8995 |
| | | | | 600/443 |

(Continued)

OTHER PUBLICATIONS

PCT International Search Report and Written Opinion issued in PCT/US2022/014906, dated Nov. 1, 2022; 11 pages.

*Primary Examiner* — Isam A Alsomiri
*Assistant Examiner* — Jonathan D Armstrong
(74) *Attorney, Agent, or Firm* — Alliance IP, LLC

(57) ABSTRACT

An apparatus, a method, and computer-implemented media. The apparatus is to receive, simultaneously, electrical signals based on respective reflected frequencies of a reflected ultrasonic waveform reflected from a target object as a result of a transmitted ultrasonic waveform; compound information from the electrical signals to generate compounded electrical signals; and cause generation of an output image on a display based on the compounded electrical signals.

5 Claims, 13 Drawing Sheets

(56) References Cited

U.S. PATENT DOCUMENTS

| | | |
|---|---|---|
| 2015/0011882 A1* | 1/2015 | Abe .................... G01S 15/8995 |
| | | 600/443 |
| 2015/0201838 A1 | 7/2015 | Gencer et al. |
| 2015/0324957 A1 | 11/2015 | Honjo et al. |
| 2016/0128675 A1* | 5/2016 | Kang .................... A61B 8/463 |
| | | 600/443 |
| 2017/0020487 A1 | 1/2017 | Chang et al. |
| 2020/0196987 A1 | 6/2020 | Kim |
| 2021/0186457 A1 | 6/2021 | Hennersperger et al. |
| 2021/0255321 A1* | 8/2021 | Shin .................... G01S 15/8906 |
| 2023/0380813 A1* | 11/2023 | Zhu .................... A61B 8/4477 |

* cited by examiner

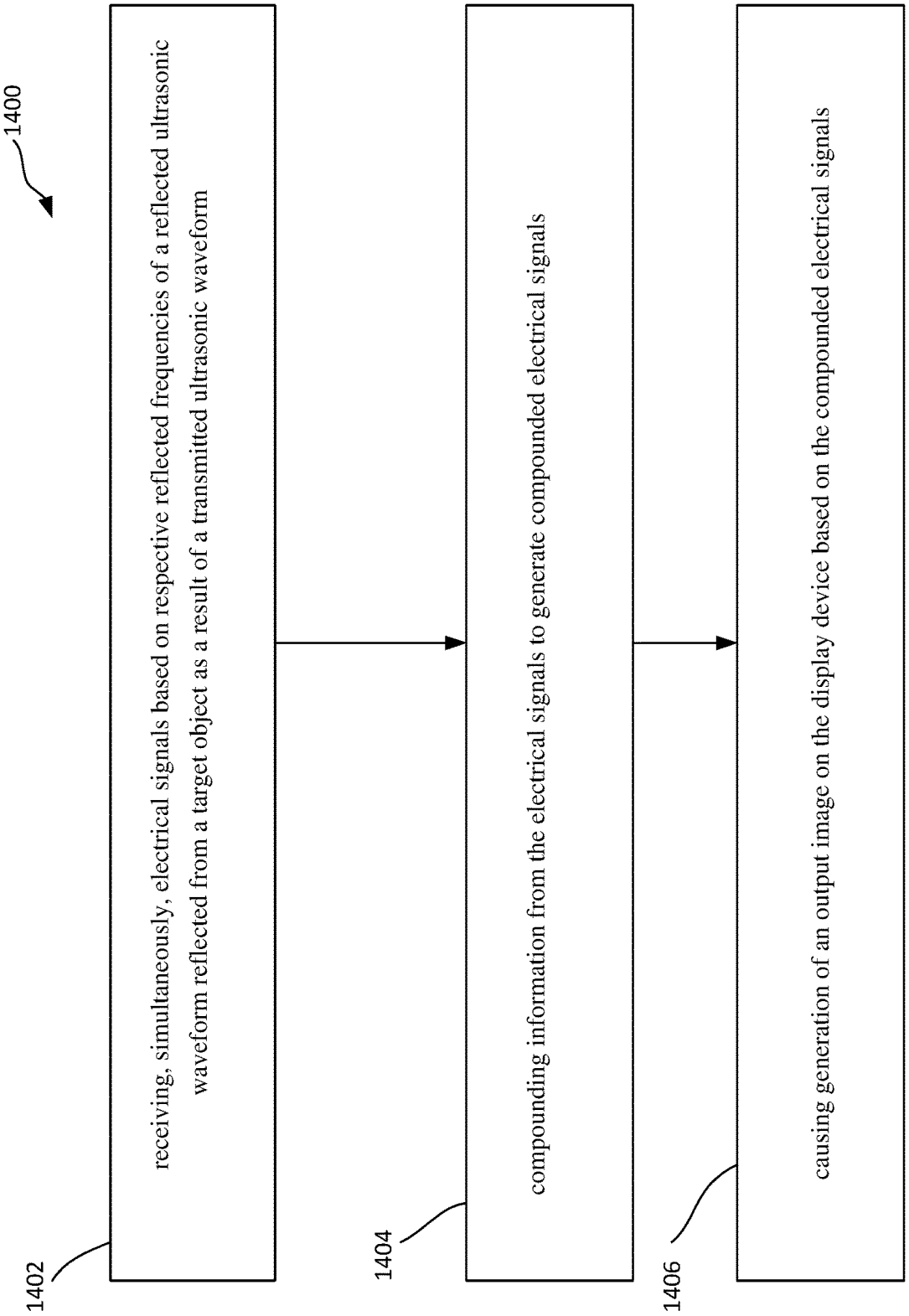

APPARATUS, SYSTEM AND METHOD TO COMPOUND SIGNALS OF RESPECTIVE RECEIVED ULTRASONIC FREQUENCIES TO GENERATE AN OUTPUT ULTRASONIC IMAGE

BACKGROUND

Field

Embodiments relate in general to the field of signal processing for imaging devices, and to the field of signal processing for ultrasound imaging devices or probes such as ones including micromachined ultrasound transducers (MUTs).

BACKGROUND

Ultrasound imaging is widely used in the fields of medicine and non-destructive testing.

An ultrasound imaging probe or ultrasonic imaging device typically includes an array of many individual ultrasonic transducers (pixels) that are used to emit and receive acoustic energy relative to a target to be imaged. A reflected waveform is received by a transducer (for example, a micro-machined ultrasonic transducer), converted to an electrical signal and, with further signal processing, an image is created. Fluid velocity and direction of fluid flow (for example, with respect to blood flow) may also be measured or detected by ultrasound and presented visually to the ultrasound imaging device operator. This quantification and visualization of anatomical structures and movement can be utilized in support of a range of medical diagnostic applications and other medical procedures.

The image quality for images obtained through the use of an ultrasonic imaging device can sometimes make it difficult to distinguish anatomical features with enough certainty. Mechanisms are needed to improve the image quality obtained by ultrasonic imaging devices.

SUMMARY

The ultrasonic imaging device of some embodiments may operate according to one or more sets of instructions, using algorithms, either collectively or individually, to assist in obtaining ultrasonic images whose quality is more reliable than those of the state of the art.

BRIEF DESCRIPTION OF THE DRAWINGS

The novel features of the invention are set forth with particularity in the appended claims. A better understanding of the features and advantages of Some embodiments will be obtained by reference to the following detailed description that sets forth illustrative embodiments, in which the principles of the invention are utilized, and the accompanying drawings (also "Figure" and "Fig." herein), of which:

FIG. 14 depicts a flowchart of a process according to some embodiment.

DETAILED DESCRIPTION

Figure 1:
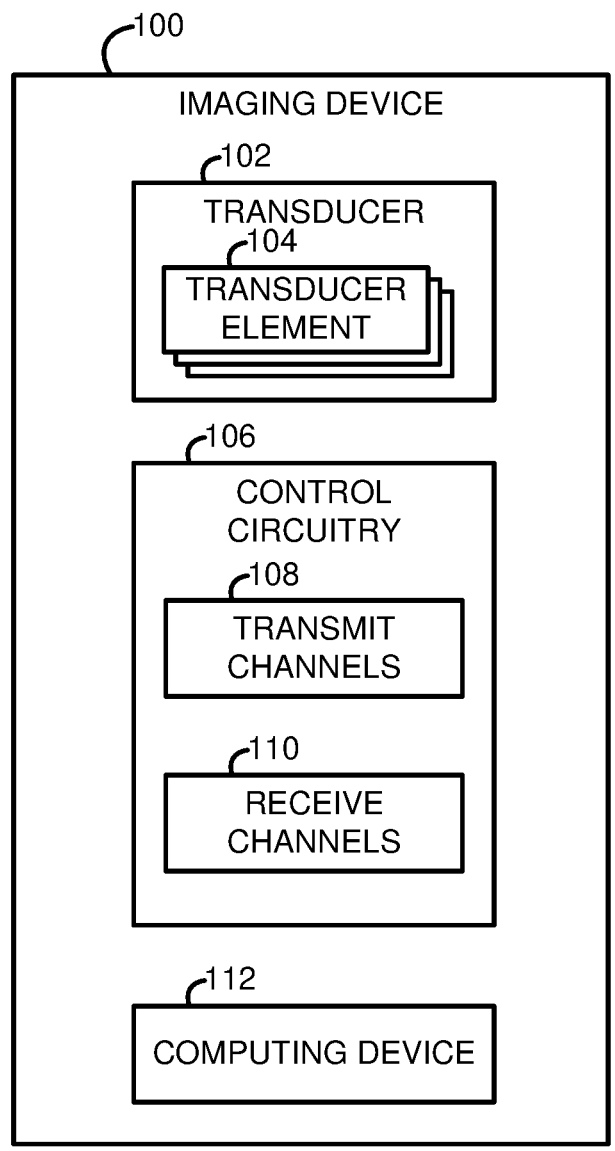
FIG. 1 is a block diagram of an imaging device with selectively alterable characteristics, in accordance with disclosed embodiments.

Some embodiments relate to an apparatus of a computing device, a computer-readable storage medium, a method, and a system. The apparatus of the computing device is to: simultaneously receive respective electrical signals that are based on respective frequencies corresponding to a reflected ultrasonic waveform reflected from a target object subjected to a transmitted ultrasonic waveform; compound information from the respective electrical signals to generate compounded electrical signals; and cause generation of an image on a display based on the compounded electrical signals.

In some embodiments, the respective frequencies are respective harmonics of a fundamental frequency, the harmonics corresponding to the reflected ultrasonic waveform, and the transmitted ultrasonic waveform is at the fundamental frequency. In such embodiments, there is a single transmit frequency, the fundamental frequency, for example 1.75 MHz.

In some embodiments, the respective frequencies are respective frequencies of the reflected ultrasonic waveform, and the transmitted ultrasonic waveform is a multimodal waveform with fundamental frequencies that correspond to the respective frequencies of the reflected ultrasonic waveform. In this embodiment, transducer elements of a transducer array of an ultrasound imaging device may be multimodal, as will be described in further detail below. As such, the transducer elements are to generate a transmitted ultrasonic waveform that is based on a number of different fundamental frequencies, such as, for example, a 1.75 MHz fundamental, a 3.5 MHz fundamental, and a 5.0 MHz fundamental.

In some embodiments, the apparatus is further to implement a predictive algorithm to use information from electrical signals corresponding to a first region of the target object to generate predictive electrical signals for a second region of the target object different from the first region; and to cause generation of the image on the display based on combined electrical signals that are a combination of the compounded electrical signals and the predictive electrical signals.

Compounding according to some embodiments may include one or more of the following, including any combination thereof: simple averaging, weighted averaging, alpha blending with depth adaptive compounding, gain-compensated compounding, adaptive compounding, predictive compounding, lateral frequency compounding and Doppler compounding. Such compounding methods will be described in further detail below.

Advantageously, some embodiments provide algorithms that allow the generation of ultrasound images that allow blending the benefit of better image resolution at deeper target object locations associated with lower frequencies of the reflected ultrasonic waveform with the benefit of better resolution at shallower penetration associated with higher frequencies of the reflected ultrasonic waveform. The latter allows the generation of images that show improved image resolution at various depths of the target object.

Some existing solutions use Tissue Harmonic Imaging (TiHI). In TiHI, a transducer generates a transmitted ultrasonic waveform at a single fundamental frequency (1.5 MHz), and the device processes the reflected ultrasonic waveform at one harmonic of the fundamental frequency of the transmitted ultrasonic waveform (transmitted ultrasonic waveform), typically at a harmonic based on two times the fundamental frequency (3.0 MHz).

Some existing solutions use Compound Harmonic Imaging (CHI).

In CHI, a transducer generates, at separate times, separate transmitted ultrasonic waveforms each at a given fundamental frequency (3.0 MHz and 3.5 MHz), and the device processes two corresponding reflected ultrasonic waveforms at the second harmonic of each of the fundamental frequencies. The processing includes compounding the two received signals, and may include some form of alpha blending, but the transmission includes multiple transmissions at different times, and the compounding is therefore not based on a reflected ultrasonic waveform that is based on a single transmission.

Reference is now made to FIGS. 1-4, which show devices and circuitries that may be used to implement some embodiments as described herein. The specific discussion of embodiments is then provided further below in the context of FIGS. 5-14.

Some embodiments relate to imaging devices, and more particularly to ultrasound imaging devices that are electronically configurable. Ultrasound imaging devices may be used to image internal tissue, bones, blood flow, or organs of human or animal bodies in a non-invasive manner. The images can then be displayed. To perform ultrasound imaging, the ultrasound imaging devices transmits an ultrasonic signal into the body and receive a reflected signal from the body part being imaged. Such ultrasound imaging devices include transducers and associated electronics, which may be referred to as transceivers or imagers, and which may be based on photo-acoustic or ultrasonic effects. Such transducers may be used for imaging and may be used in other applications as well. For example, the transducers may be used in medical imaging; flow measurements in pipes, speaker, and microphone arrays; lithotripsy; localized tissue heating for therapeutic; and highly intensive focused ultrasound (HIFU) surgery.

Additional aspects and advantages of some embodiments will become readily apparent to those skilled in this art from the instant detailed description, wherein only illustrative embodiments are shown and described. As will be realized, some embodiments are capable of achieving other, different goals, and their several details are capable of modifications in various obvious respects, all without departing from the disclosure. Accordingly, the drawings and description are to be regarded as illustrative in nature, and not as restrictive.

Traditionally, imaging devices such as ultrasound imagers used in medical imaging use piezoelectric (PZT) materials or other piezo ceramic and polymer composites. Such imaging devices may include a housing to house the transducers with the PZT material, as well as other electronics that form and display the image on a display unit. To fabricate the bulk PZT elements or the transducers, a thick piezoelectric material slab may be cut into large rectangular shaped PZT elements. These rectangular-shaped PZT elements may be expensive to build, since the manufacturing process involves precisely cutting generally the rectangular-shaped thick PZT or ceramic material and mounting it on substrates with precise spacing. Further, the impedance of the transducers is much higher than the impedance of the transmit/receive electronics for the transducers, which can affect performance.

Still further, such thick bulk PZT elements can require very high voltage pulses, for example 100 volts (V) or more to generate transmission signals. This high drive voltage results in high power dissipation, since the power dissipation in the transducers is proportional to the square of the drive voltage. This high power dissipation generate heat within the imaging device such that cooling arrangements are necessitated. These cooling systems increase the manufacturing costs and weights of the imaging devices which makes the imaging devices more burdensome to operate.

Even further, the transmit/receive electronics for the transducers may be located far away from the transducers themselves, thus requiring micro-coax cables between the transducers and transmit/receive electronics. In general, the cables have a precise length for delay and impedance matching, and, quite often, additional impedance matching networks are used for efficient connection of the transducers through the cables to the electronics.

Some embodiments may be utilized in the context of imaging devices that utilize either piezoelectric micromachined ultrasound transducer (pMUT) or capacitive micromachine ultrasonic transducer (cMUT) technologies, as described in further detail herein.

In general, MUTs, such as both cMUT and pMUT, include a diaphragm (a thin membrane attached at its edges, or at some point in the interior of the probe), whereas a "traditional," bulk PZT element typically consists of a solid piece of material.

Piezoelectric micromachined ultrasound transducers (pMUTs) may be efficiently formed on a substrate leveraging various semiconductor wafer manufacturing operations. Semiconductor wafers may currently come in 6 inch, 8 inch, and 12 inch sizes and are capable of housing hundreds of transducer arrays. These semiconductor wafers start as a silicon substrate on which various processing operations are performed. An example of such an operation is the formation of $SiO_2$ layers, also known as insulating oxides. Various other operations such as the addition of metal layers to serve as interconnects and bond pads are performed to allow connection to other electronics. Yet another example of a machine operation is the etching of cavities. Compared to the conventional transducers having bulky piezoelectric material, pMUT elements built on semiconductor substrates are less bulky, are cheaper to manufacture, and have simpler and higher performance interconnection between electronics and transducers. As such, they provide greater flexibility in the operational frequency of the imaging device using the same, and potential to generate higher quality images.

In some embodiments, the imaging device is coupled to an application specific integrated circuit (ASIC) that includes transmit drivers, sensing circuitry for received echo signals, and control circuitry to control various operations. The ASIC may be formed on another semiconductor wafer. This ASIC may be placed in close proximity to pMUT or cMUT elements to reduce parasitic losses. As a specific example, the ASIC may be 50 micrometers (μm) or less away from the transducer array. In a broader example, there may be less than 100 μm separation between the 2 wafers or 2 die, where each wafer includes many die and a die includes a transducer in the transducer wafer and an ASIC in the ASIC wafer. In some embodiments, the ASIC has matching dimensions relative to the pMUT or cMUT array and allows the devices to be stacked for wafer-to-wafer interconnection or transducer die on ASIC wafer or transducer die to ASIC die interconnection. Alternatively, the transducer can also be developed on top of the ASIC wafer using low temperature piezo material sputtering and other low temperature processing compatible with ASIC processing.

Wherever the ASIC and the transducer interconnect, according to one embodiment, the two may have similar footprints. More specifically, according to the latter embodiment, a footprint of the ASIC may be an integer multiple or divisor of the MUT footprint.

Regardless of whether the imaging device is based on pMUT or cMUT, an imaging device according to some embodiments may include a number of transmit channels and a number of receive channels. Transmit channels are to drive the transducer elements with a voltage pulse at a frequency the elements are responsive to. This causes an ultrasonic waveform to be emitted from the elements, which waveform is to be directed towards an object to be imaged (target object), such as toward an organ or other tissue in a body. In some examples, the imaging device with the array of transducer elements may make mechanical contact with the body using a gel in between the imaging device and the body. The ultrasonic waveform travels towards the object, i.e., an organ, and a portion of the waveform is reflected back to the transducer elements in the form of received/reflected ultrasonic energy where the received ultrasonic energy may converted to an electrical energy within the imaging device. The received ultrasonic energy may then be further processed by a number of receive channels to convert the received ultrasonic energy to electrical signals, and the electrical signals may be processed by other circuitry to develop an image of the object for display based on the electrical signals.

An embodiment of an ultrasound imaging device includes a transducer array, and control circuitry including, for example, an application-specific integrated circuit (ASIC), and transmit and receive beamforming circuitry, and optionally additional control electronics.

An imaging device incorporating features of the embodiments may advantageously reduce or resolve issues In an embodiment, an imaging device may include a handheld casing where transducers and associated electronic circuitries, such as a control circuitry and optionally a computing device are housed. The imaging device may also contain a battery to power the electronic circuitries.

Thus, some embodiments pertain to a portable imaging device utilizing either pMUT elements or cMUT elements in a 2D array. In some embodiments, such an array of transducer elements is coupled to an application specific integrated circuit (ASIC) of the imaging device.

In the following description, for purposes of explanation, specific details are set forth in order to provide an understanding of the disclosure. It will be apparent, however, to one skilled in the art that the disclosure may be practiced without these details. Furthermore, one skilled in the art will recognize that examples of the present disclosure, described below, may be implemented in a variety of ways, such as a process, one or more processors (processing circuitry) of a control circuitry, one or more processors (or processing circuitry) of a computing device, a system, a device, or a method on a tangible computer-readable medium.

One skilled in the art shall recognize: (1) that certain fabrication operations may optionally be performed; (2) that operations may not be limited to the specific order set forth herein; and (3) that certain operations may be performed in different orders, including being done contemporaneously.

Elements/components shown in diagrams are illustrative of exemplary embodiments and are meant to avoid obscuring the disclosure. Reference in the specification to "one example," "preferred example," "an example," "examples," "an embodiment," "some embodiments," or "embodiments" means that a particular feature, structure, characteristic, or function described in connection with the example is included in at least one example of the disclosure and may be in more than one example. The appearances of the phrases "in one example," "in an example," "in examples," "in an embodiment," "in some embodiments," or "in embodiments" in various places in the specification are not necessarily all referring to the same example or examples. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

Turning now to the figures, FIG. 1 is a block diagram of an imaging device 100 with a controller or control circuitry 106 controlling selectively alterable channels (108, 110) and having imaging computations performed on a computing device 112 according to principles described herein. As described above, the imaging device 100 may be used to generate an image of internal tissue, bones, blood flow, or organs of human or animal bodies. Accordingly, the imaging device 100 may transmit a signal into the body and receive a reflected signal from the body part being imaged. Such imaging devices may include either pMUT or cMUT, which may be referred to as transducers or imagers, which may be based on photo-acoustic or ultrasonic effects. The imaging device 100 may be used to image other objects as well. For example, the imaging device may be used in medical imaging; flow measurements in pipes, speaker, and microphone arrays; lithotripsy; localized tissue heating for therapeutic; and highly intensive focused ultrasound (HIFU) surgery.

In addition to use with human patients, the imaging device 100 may be used to acquire an image of internal organs of an animal as well. Moreover, in addition to imaging internal organs, the imaging device 100 may also be used to determine direction and velocity of blood flow in arteries and veins as in Doppler mode imaging and may also be used to measure tissue stiffness.

The imaging device 100 may be used to perform different types of imaging. For example, the imaging device 100 may be used to perform one-dimensional imaging, also known as A-Scan, two-dimensional imaging, also known as B scan, three-dimensional imaging, also known as C scan, and Doppler imaging (that is, the use of Doppler ultrasound to determine movement, such as fluid flow within a vessel). The imaging device 100 may be switched to different imaging modes, including without limitation linear mode and sector mode, and electronically configured under program control.

To facilitate such imaging, the imaging device 100 includes one or more ultrasound transducers 102, each transducer 102 including an array of ultrasound transducer elements 104. Each ultrasound transducer element 104 may be embodied as any suitable transducer element, such as a pMUT or cMUT element. The transducer elements 104 operate to 1) generate the ultrasonic pressure waves that are to pass through the body or other mass and 2) receive reflected waves (received ultrasonic energy) off the object within the body, or other mass, to be imaged. In some examples, the imaging device 100 may be configured to simultaneously transmit and receive ultrasonic waveforms or ultrasonic pressure waves (pressure waves in short). For example, control circuitry 106 may be configured to control certain transducer elements 104 to send pressure waves toward the target object being imaged while other transducer elements 104, at the same time, receive the pressure waves/ultrasonic energy reflected from the target object, and generate electrical charges based on the same in response to the received waves/received ultrasonic energy/received energy.

In some examples, each transducer element 104 may be configured to transmit or receive signals at a certain frequency and bandwidth associated with a center frequency, as well as, optionally, at additional center frequencies and bandwidths. Such multi-frequency transducer elements 104 may be referred to as multi-modal elements 104 and can expand the bandwidth of the imaging device 100. The transducer element 104 may be able to emit or receive signals at any suitable center frequency, such as about 0.1 to about 100 megahertz. The transducer element 104 may be configured to emit or receive signals at one or more center frequencies in the range from about 1.75 to about 5 megahertz.

To generate the pressure waves, the imaging device 100 may include a number of transmit (Tx) channels 108 and a number of receive (Rx) channels 110. The transmit channels 108 may include a number of components that drive the transducer 102, i.e., the array of transducer elements 104, with a voltage pulse at a frequency that they are responsive to. This causes an ultrasonic waveform to be emitted from the transducer elements 104 towards an object to be imaged.

According to some embodiments, an ultrasonic waveform may include one or more ultrasonic pressure waves transmitted from one or more corresponding transducer elements of the imaging device substantially simultaneously.

The ultrasonic waveform travels towards the object to be imaged and a portion of the waveform is reflected back to the transducer 102, which converts it to an electrical energy through a piezoelectric effect. The receive channels 110 collect electrical energy thus obtained, and process it, and send it for example to the computing device 112, which develops or generates an image that may be displayed.

In some examples, while the number of transmit channels 108 and receive channels 110 in the imaging device 100 may remain constant, and the number of transducer elements 104 that they are coupled to may vary. A coupling of the transmit and receive channels to the transducer elements may be, in one embodiment, controlled by control circuitry 106. In some examples, for example as shown in FIG. 1, the control circuitry may include the transmit channels 108 and the receive channels 110. For example, the transducer elements 104 of a transducer 102 may be formed into a two-dimensional spatial array with N columns and M rows. In a specific example, the two-dimensional array of transducer elements 104 may have 128 columns and 32 rows. In this example, the imaging device 100 may have up to 128 transmit channels 108 and up to 128 receive channels 110. In this example, each transmit channel 108 and receive channel 110 may be coupled to multiple or single pixels 104. For example, depending on the imaging mode (for example, whether a linear mode where a number of transducers transmit ultrasound waves in a same spatial direction, or a sector mode, where a number of transducers transmit ultrasound waves in different spatial directions), each column of transducer elements 104 may be coupled to a single transmit channel 108 and a single receive channel (110). In this example, the transmit channel 108 and receive channel 110 may receive composite signals, which composite signals combine signals received at each transducer element 104 within the respective column. In another example, i.e., during a different imaging mode, each transducer element 104 may be coupled to its dedicated transmit channel 108 and its dedicated receive channel 110. In some embodiments, a transducer element 104 may be coupled to both a transmit channel 108 and a receive channel 110. For example, a transducer element 104 may be adapted to create and transmit an ultrasound pulse and then detect the echo of that pulse in the form of converting the reflected ultrasonic energy into electrical energy.

The control circuitry 106 may be embodied as any circuit or circuits configured to perform the functions described herein. For example, the control circuitry 106 may be embodied as or otherwise include an application specific integrated circuit (ASIC), a field programmable gate array (FPGA), a system-on-a-chip, a processor and memory, a voltage source, a current source, one or more amplifiers, one or more digital-to-analog converters, one or more analog-to-digital converters, etc.

The illustrative computing device 112 may be embodied as any suitable computing device including any suitable components, such as one or more processors, memory circuitry, communication circuitry, battery, display, etc. In one embodiment, the computing device 112 may be integrated with the control circuitry 106, transducers 102, etc., into a single package or single chip, or a single system on a chip (SoC), as suggested for example in the embodiment of FIG. 1. In other embodiments, some or all of the computing devices may be in a separate package from the control circuitry, and the transducers, etc., as suggested for example in the embodiment of in FIG. 2 as will be described in further detail below.

Each transducer element may have any suitable shape such as, square, rectangle, ellipse, or circle. The transducer elements may be arranged in a two dimensional array arranged in orthogonal directions, such as in N columns and M rows as noted herein, or may be arranged in an asymmetric (or staggered) rectilinear array.

Transducer elements 104 may have associated transmit driver circuits of associated transmit channels, and low noise amplifiers of associated receive channels. Thus, a transmit channel may include transmit drivers, and a receive channel may include one or more low noise amplifiers. For example, although not explicitly shown, the transmit and receive channels may each include multiplexing and address control circuitry to enable specific transducer elements and sets of transducer elements to be activated, deactivated or put in low power mode. It is understood that transducers may be arranged in patterns other than orthogonal rows and columns, such as in a circular fashion, or in other patterns based on the ranges of ultrasonic waveforms to be generated therefrom.

Figure 2:
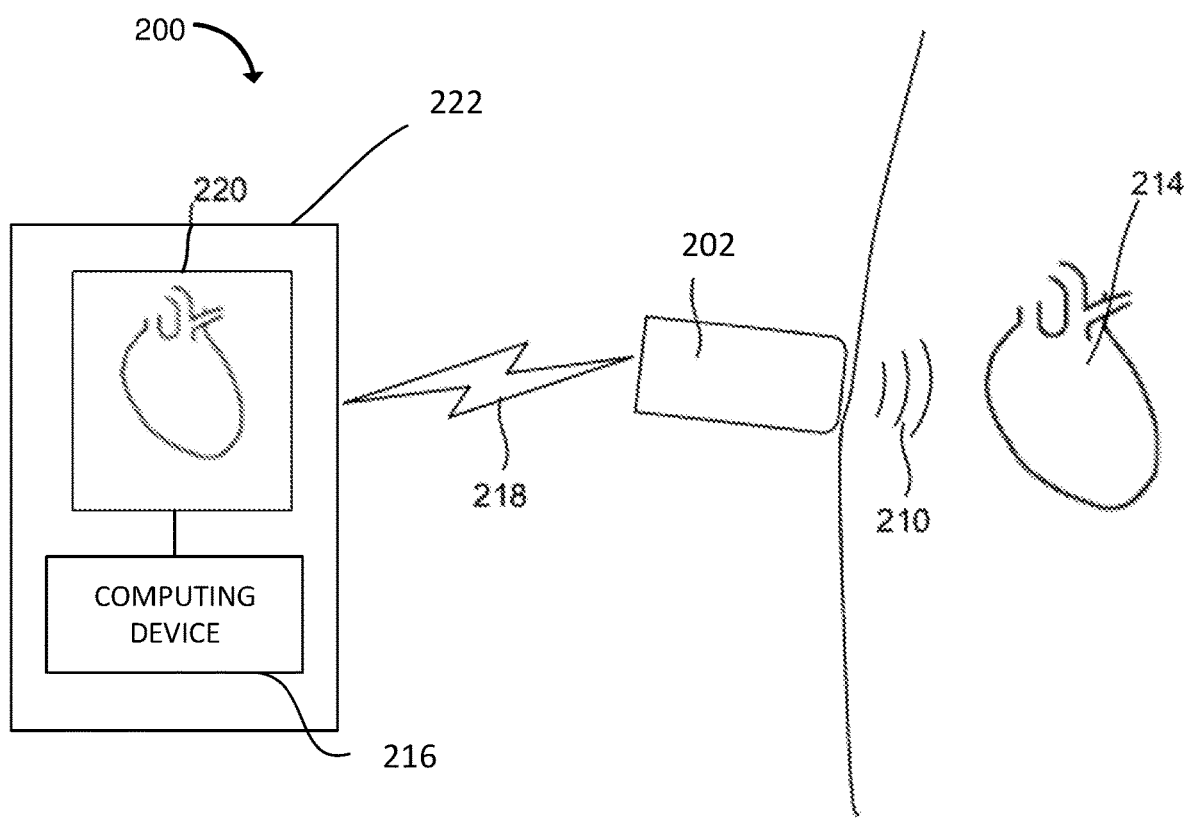
FIG. 2 is a diagram of an imaging system with selectively alterable characteristics, in accordance with disclosed embodiments.

FIG. 2 is a diagram of an imaging environment including an imaging system with selectively configurable characteristics, according to an embodiment. The imaging system of FIG. 2 may include an imaging device 202 and a computing system 222 which includes a computing device 216 and a display 220 coupled to the computing device, as will be described in further detail below.

As depicted in FIG. 2, the computing device 216 may, according to one embodiment, and unlike the embodiment of FIG. 1, be physically separate from the imaging device 220. For example, the computing device 216 and display device 220 may be disposed within a separate device (in this context, the shown computing system 222, physically separate from imaging device 202 during operation) as compared with the components of the imaging device 202. The computing system 222 may include a mobile device, such as cell phone or tablet, or a stationary computing device, which can display images to a user. In another example, as shown in FIG. 1 for example, the display device, the computing device, and associated display, may be part of the imaging device 202 (now shown). That is, the imaging device 100, computing device 216, and display device 220 may be disposed within a single housing.

A "computing device" as referred to herein may, in some embodiments, be configured to generate signals to at least one of cause an image of the object to be displayed on a display, or cause information regarding the image to be communicated to a user.

As depicted, the imaging system includes the imaging device 202 that is configured to generate and transmit, via the transmit channels (FIG. 1, 108), pressure waves 210 toward an object, such as a heart 214, in a transmit mode/process. The internal organ, or other object to be imaged, may reflect a portion of the pressure waves 210 toward the imaging device 202 which may receive, via a transducer (such as transducer 102 of FIG. 1), receive channels (FIG. 1, 110), control circuitry (FIG. 1, 106), the reflected pressure waves. The transducer may generate an electrical signal based on the received ultrasonic energy in a receive mode/process. A transmit mode or receive mode may be applicable in the context of imaging devices that may be configured to either transmit or receive, but at different times. However, as noted previously, some imaging devices according to embodiments may be adapted to be in both a transmit mode and a receive mode simultaneously. The system also includes a computing device 216 that is to communicate with the imaging device 100 through a communication channel, such as a wireless communication channel 218 as shown, although embodiments also encompass within their scope wired communication between a computing system and imaging device. The imaging device 100 may communicate signals to the computing device 216 which may have one or more processors to process the received signals to complete formation of an image of the object. A display device 220 of the computing system 222 may then display images of the object using the signals from the computing device. The computing system may further convey information to a user regarding a defective pixel as noted above.

An imaging device according to some embodiments may include a portable device, and/or a handheld device that is adapted to communicate signals through a communication channel, either wirelessly (using a wireless communication protocol, such as an IEEE 802.11 or Wi-Fi protocol, a Bluetooth protocol, including Bluetooth Low Energy, a mmWave communication protocol, or any other wireless communication protocol as would be within the knowledge of a skilled person) or via a wired connection such as a cable (such as USB2, USB 3, USB 3.1, and USB-C) or such as interconnects on a microelectronic device, with the computing device. In the case of a tethered or wired, connection, the imaging device may include a port as will be described in further detail in the context of FIG. 3 for receiving a cable connection of a cable that is to communicate with the computing device. In the case of a wireless connection, the imaging device 100 may include a wireless transceiver to communicate with the computing device 216.

It should be appreciated that, in various embodiments, different aspects of the disclosure may be performed in different components. For example, in one embodiment, the imaging device may include circuitry (such as the channels) to cause ultrasound waveforms to be sent and received through its transducers, while the computing device may be adapted to control such circuitry to the generate ultrasound waveforms at the transducer elements of the imaging device using voltage signals, and further a processing of the received ultrasonic energy.

Figure 3:
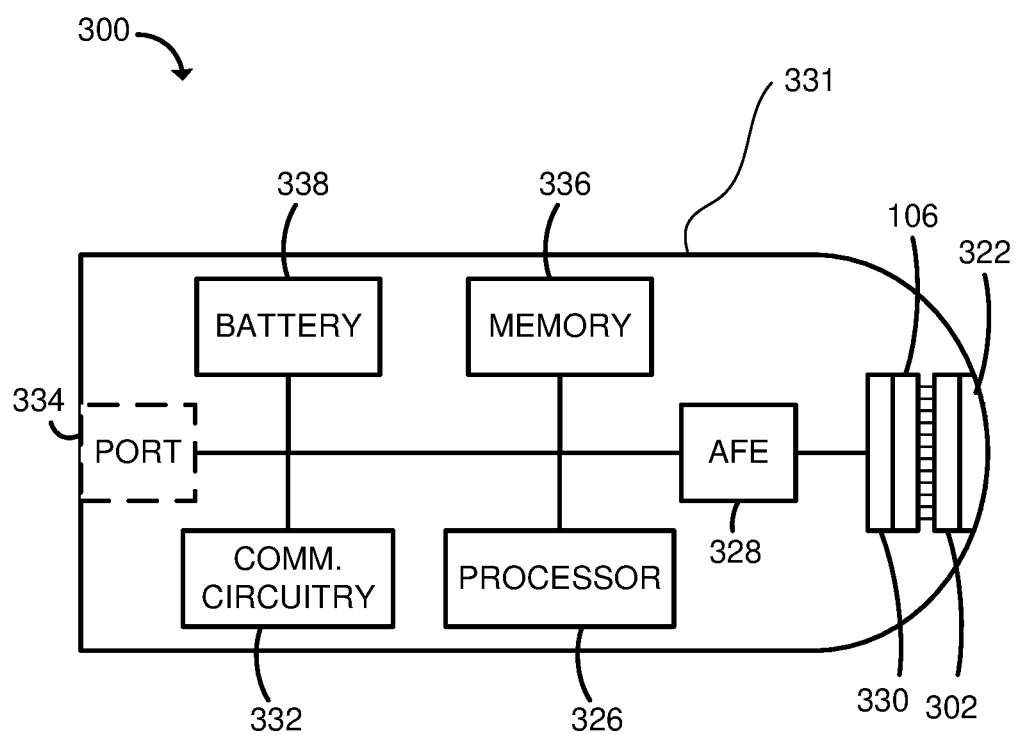
FIG. 3 is a schematic diagram of an imaging device with selectively alterable characteristics, in accordance with disclosed embodiments.

FIG. 3 represents a view of an imaging device according to some embodiments, as will be described in further detail below.

As seen in FIG. 3, the imaging device 300 may include a handheld casing 331 where transducers 302 and associated electronics are housed. The imaging device may also contain a battery 338 to power the electronics. FIG. 3 thus shows an embodiment of a portable imaging device capable of 2D and 3D imaging using pMUTs in a 2D array, optionally built on a silicon wafer. Such an array coupled to an application specific integrated circuit (ASIC) 106 with electronic configuration of certain parameters, enables a higher quality of image processing at a low cost than has been previously possible. Further by controlling certain parameters, for example the number of channels used, power consumption may be altered and temperature may be changed.

The imaging device 300 according to some embodiments is configured to allow system configurability and adaptability in real time based on information regarding one or more defective pixels (defective pixel data). This is done for example by comparing a current pixel performance dataset of one or more pixels of a transducer array of an imaging device with a baseline pixel performance dataset of the same pixels as will be explained in further detail below.

Now addressing FIG. 3 in more detail, FIG. 3 is a schematic diagram of an imaging device 300 with selectively adjustable features, according to some embodiments. The imaging device 300 may be similar to imaging device 100 of FIG. 1, or to imaging device 202 of FIG. 2, by way of example only. As described above, the imaging device may include an ultrasonic medical probe. FIG. 3 depicts transducer(s) 302 of the imaging device 300. As described above, the transducer(s) 302 may include arrays of transducer elements (FIG. 1, 104) that are adapted to transmit and receive pressure waves (FIG. 2, 210). In some examples, the imaging device 300 may include a coating layer 322 that serves as an impedance matching interface between the transducers 302 and the human body, or other mass or tissue through which the pressure waves (FIG. 2, 210) are transmitted. In some cases, the coating layer 322 may serve as a lens when designed with the curvature consistent with focal length desired.

The imaging device 300 may be embodied in any suitable form factor. In some embodiments, part of the imaging device 300 that includes the transducers 302 may extend outward from the rest of the imaging device 100. The imaging device 300 may be embodied as any suitable ultrasonic medical probe, such as a convex array probe, a micro-convex array probe, a linear array probe, an endovaginal probe, endorectal probe, a surgical probe, an intraoperative probe, etc.

In some embodiments, the user may apply gel on the skin of a living body before a direct contact with the coating layer 322 so that the impedance matching at the interface between the coating layer 322 and the human body may be improved. Impedance matching reduces the loss of the pressure waves (FIG. 2, 210) at the interface and the loss of the reflected wave travelling toward the imaging device 300 at the interface.

In some examples, the coating layer 322 may be a flat layer to maximize transmission of acoustic signals from the transducer(s) 102 to the body and vice versa. The thickness of the coating layer 322 may be a quarter wavelength of the pressure wave (FIG. 2, 210) to be generated at the transducer(s) 102.

The imaging device 300 also includes a control circuitry 106, such as one or more processors, optionally in the form of an application-specific integrated circuit (ASIC chip or ASIC), for controlling the transducers 102. The control circuitry 106 may be coupled to the transducers 102, such as by way of bumps. As described above, the transmit channels 108 and receive channels 110 may be selectively alterable or adjustable, meaning that the quantity of transmit channels 108 and receive channels 110 that are active at a given time may be altered such that, for example, one or more pixels determined to be defective are not used. For example, the control circuitry 106 may be adapted to selectively adjust the transmit channels 108 and receive channel 110 based on pixels to be tested for defects, and/or based on pixels determined to be defective.

In some examples, the basis for altering the channels may be a mode of operation, the mode of operation may in turn be chosen based on which pixels are determined to be defective, and optionally based on the type of defect of each defective pixel.

The imaging device may also include one or more processors 326 for controlling the components of the imaging device 100. One or more processors 326 may be configured to, in addition to control circuitry 106, at least one of control an activation of transducer elements, process electrical signals based on reflected ultrasonic waveforms from the transducer elements or generate signals to cause generation of an image of an object being imaged by one or more processors of a computing device, such as computing device 112 of FIG. 1 or 216 of FIG. 2. One or more processors 326 may further be adapted to perform other processing functions associated with the imaging device. The one or more processors 326 may be embodied as any type of processors 326. For example, the one or more processors 326 may be embodied as a single or multi-core processor(s), a single or multi-socket processor, a digital signal processor, a graphics processor, a neural network compute engine, an image processor, a microcontroller, a field programmable gate array (FPGA), or other processor or processing/controlling circuit. The imaging device 100 may also include circuit(s) 328, such as Analog Front End (AFE), for processing/conditioning signals, and an acoustic absorber layer 330 for absorbing waves that are generated by the transducers 102 and propagated towards the circuits 328. That is, the transducer(s) 102 may be mounted on a substrate and may be attached to an acoustic absorber layer 330. This layer absorbs any ultrasonic signals that are emitted in the reverse direction (i.e., in a direction away from coating layer 322 in a direction toward port 334), which may otherwise be reflected and interfere with the quality of the image. While FIG. 3 depicts the acoustic absorber layer 330, this component may be omitted in cases where other components prevent a material transmission of ultrasound in the reverse direction.

The analog front end 328 may be embodied as any circuit or circuits configured to interface with the control circuitry 106 and other components of the imaging device, such as the processor 326. For example, the analog front end 328 may include, e.g., one or more digital-to-analog converters, one or more analog-to-digital converters, one or more amplifiers, etc.

The imaging device may include a communication unit 332 for communicating data, including control signals, with an external device, such as the computing device (FIG. 2, 216), through for example a port 334 or a wireless transceiver. The imaging device 100 may include memory 336 for storing data. The memory 336 may be embodied as any type of volatile or non-volatile memory or data storage capable of performing the functions described herein. In operation, the memory 336 may store various data and software used during operation of the imaging device 100 such as operating systems, applications, programs, libraries, and drivers.

In some examples, the imaging device 100 may include a battery 338 for providing electrical power to the components of the imaging device 100. The battery 338 may also include battery charging circuits which may be wireless or wired charging circuits (not shown). The imaging device may include a gauge that indicates a battery charge consumed and is used to configure the imaging device to optimize power management for improved battery life. Additionally or alternatively, in some embodiments, the imaging device may be powered by an external power source, such as by plugging the imaging device into a wall outlet.

Figure 4:
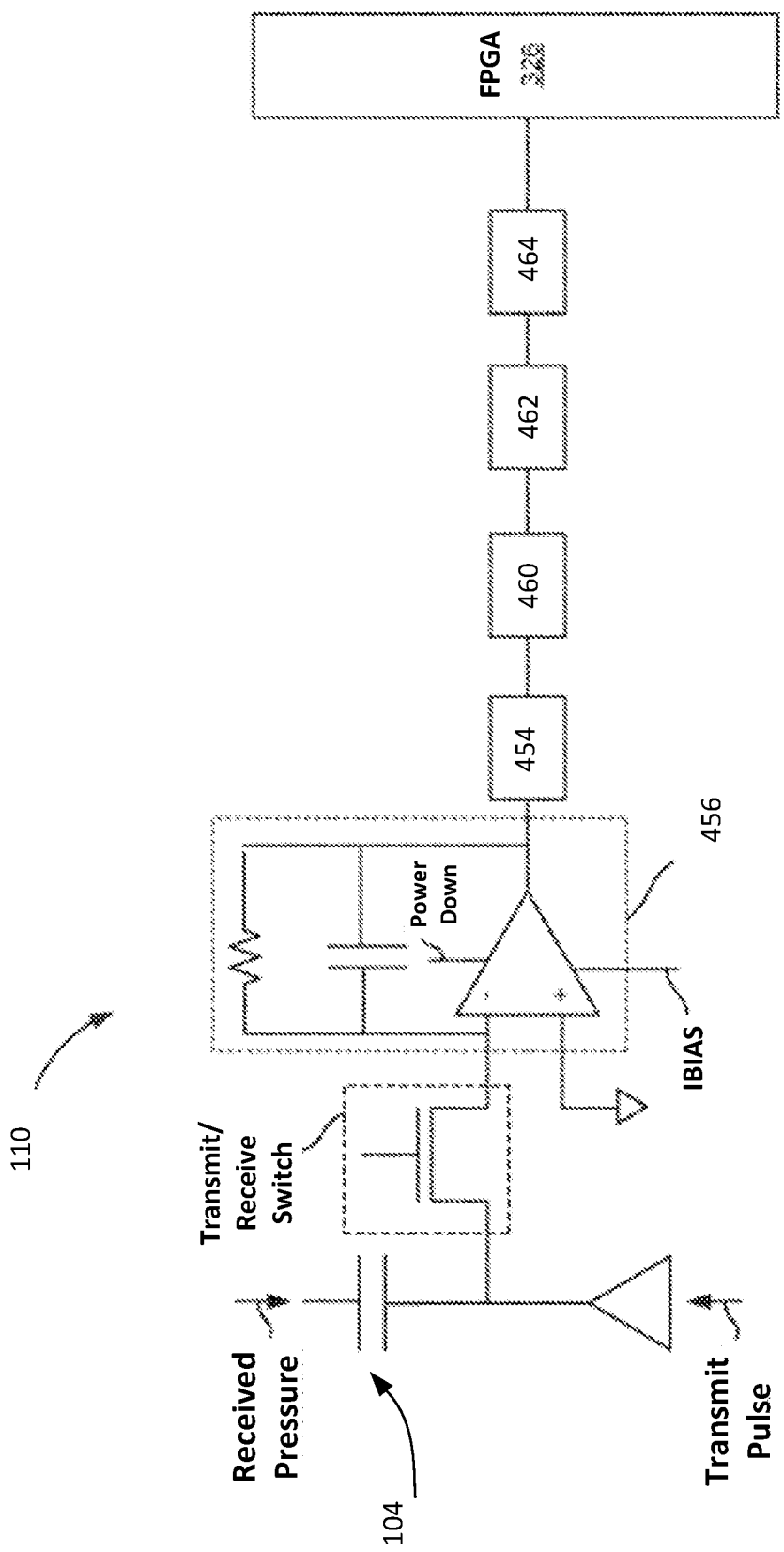
FIG. 4 depicts a receive channel, according to an example of the principles described herein.

FIG. 4 depicts a receive channel 110, according to an example of the principles described herein. The receive channel 110 is coupled to a transducer element (FIG. 1, 104) to receive the reflected pressure wave (FIG. 2, 210). FIG. 4 also depicts the connection between the transducer element (FIG. 1, 104) and the transmit channel (FIG. 1, 110). In one example, the transmit channel (FIG. 1, 108) goes towards a high impedance during a receive operation at the node where the received pressure and transmitted pulse meet. Specifically, the reflected pressure wave is converted to an electrical charge in the transducer element 104 and this is converted to a voltage by a low noise amplifier (LNA) (456). The LNA (456) is a charge amplifier, where charge is converted to an output voltage. In some examples, the LNA (456) has programmable gain, where the gain can be changed in real time.

The LNA (456) converts charge in the transducer to a voltage output and also amplifies the received echo signal. A switch (transmit/receive switch) connects the LNA (456) to the transducer element 104 in the receive mode of operation.

The output of this LNA (456) then is connected to other components to condition the signal. For example, a programmable gain amplifier (PGA) (458) adjusts the magnitude of the voltage and provides a way to change the gain as a function of time and may be known as a time gain amplifier (TGA). As the signal travels deeper into the tissue, it is attenuated.

Accordingly, a larger gain is used to compensate, which larger gain is implemented by the TGA. The bandpass filter 460 operates to filter out noise and out of band signals. An analog to digital converter (ADC) 462 digitizes the analog signal to convert the signal to the digital domain such that further processing can be done digitally. Data from the ADC 462 is then digitally processed at a demodulation unit 464 and passed to the FPGA 326 to generate a scan line. In some implementations, the demodulation unit 464 can be implemented elsewhere, for example in the FPGA. The demodulation unit frequency-shifts the carrier signal to baseband with two components in quadrature (I and Q), for further digital processing in some examples, the analog to digital converter (ADC) 462 may implement a successive-approximation-register (SAP) architecture to reduce latency of the ADC 462. That is, as the ADC 462 is turned off and on repeatedly, it needs to have little to no latency so as to not delay signal processing following turning on.

Figure 6:
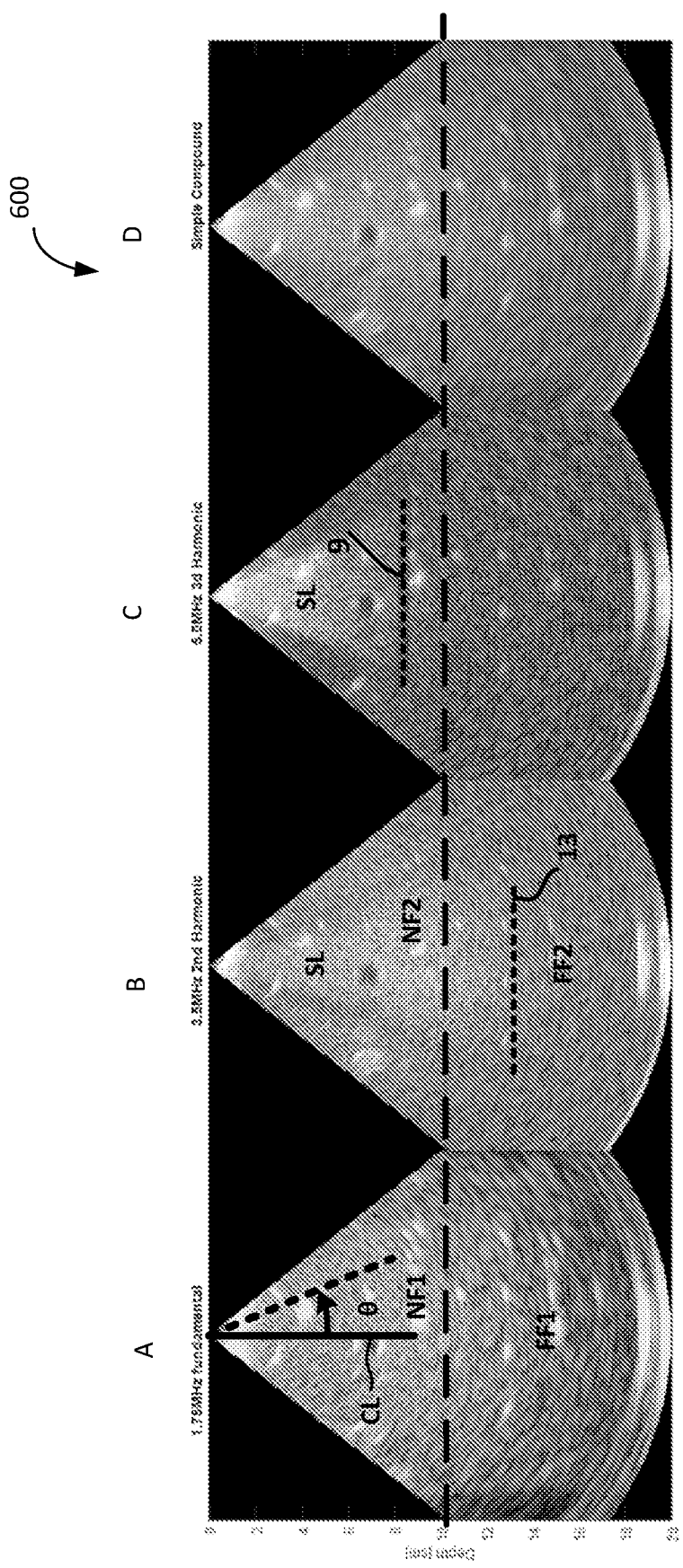
FIG. 6 shows a set of four respective ultrasonic images of a target object, where an output image D is obtained through simple averaging of pixel irradiances of images A-C, where each of images A-C corresponds to a different reflected frequency.
Figure 7:
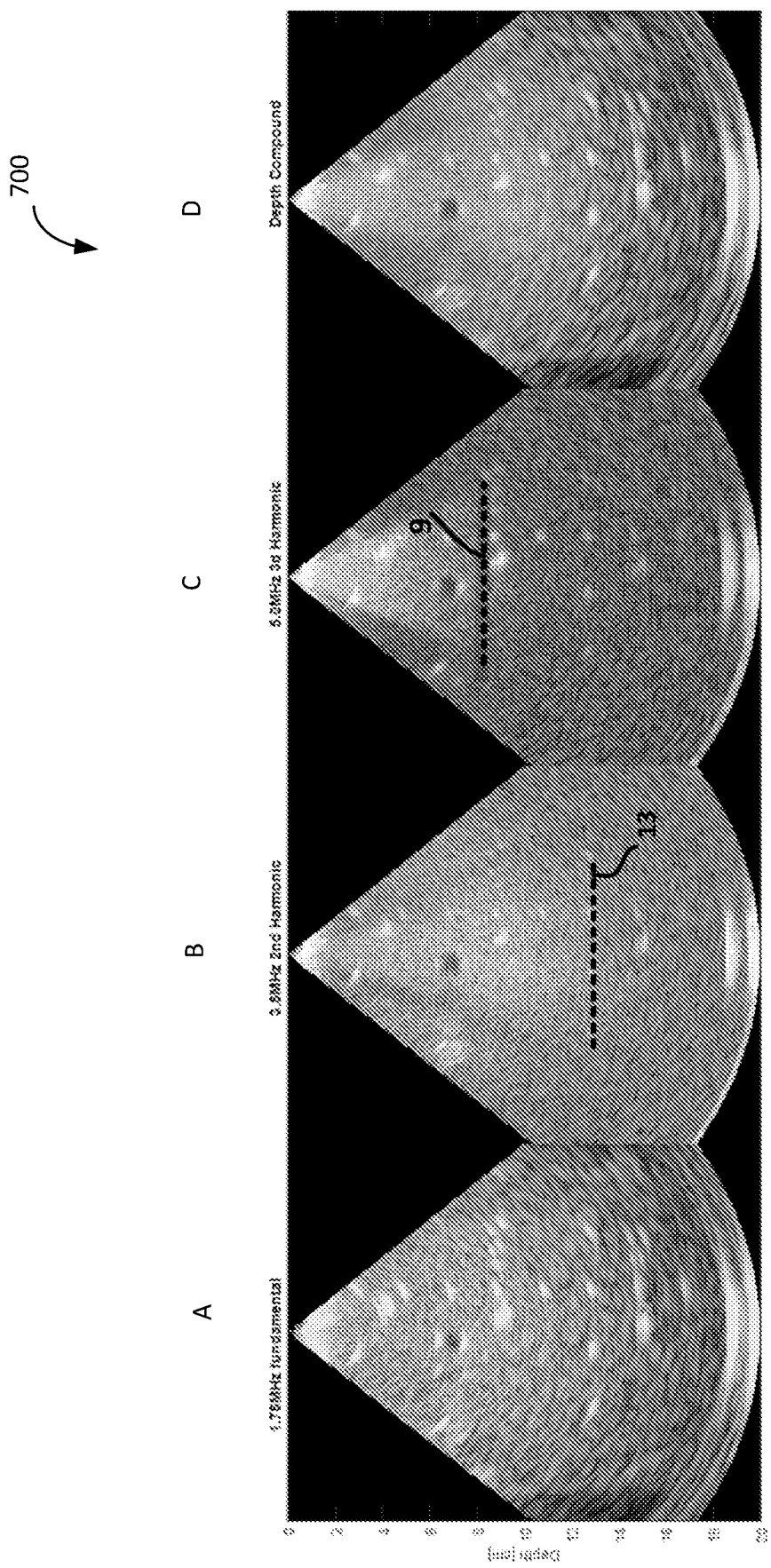
FIG. 7 shows a set of four respective ultrasonic images of a target object, where an output image D, is obtained through alpha blending using depth adaptive compounding (DAC) of pixel irradiances of images A-C corresponding to three respective reflected frequencies.
Figure 10:
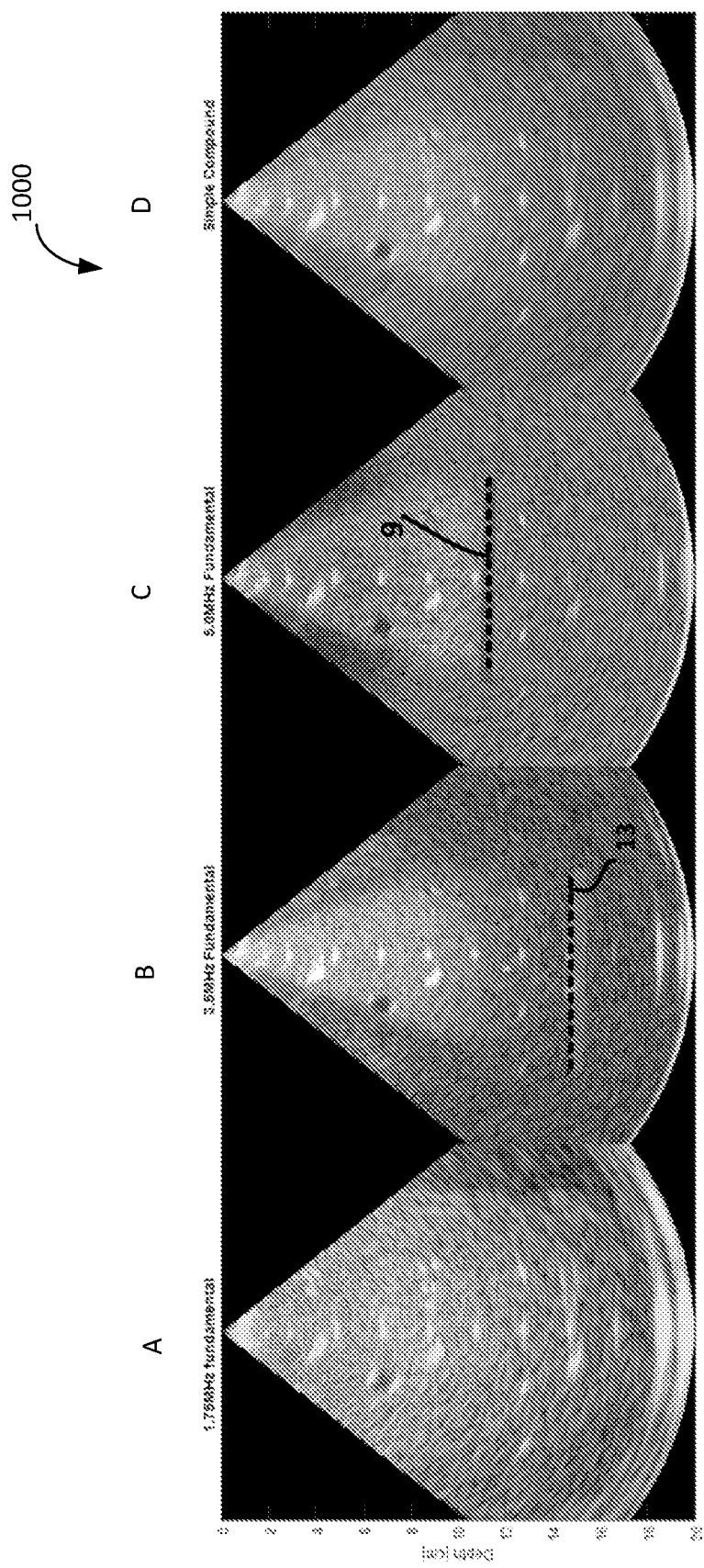
FIG. 10 is a set of images similar to those of FIG. 6, but using the pulse of FIGS. 9A and 9B to generate the images A-C, and further using simple compounding to generate the compound image D.

Some embodiments aim to leverage the broad band of transducer elements of a transducer array, such as those described above, by effectively generating a transmitted ultrasonic waveform at a low frequency pulse, low fundamental frequency, and imaging at the harmonics of the single fundamental frequency. In a tri-harmonic imaging (THI) implementation, the first through third harmonics may for example be used to generate, substantially simultaneously, the respective electrical signals representative of the reflected ultrasonic waveform. FIGS. 6, 7 and 10 are representative figures that depict THI according to some embodiments. These figures will be explained in detail further below.

Figure 11:
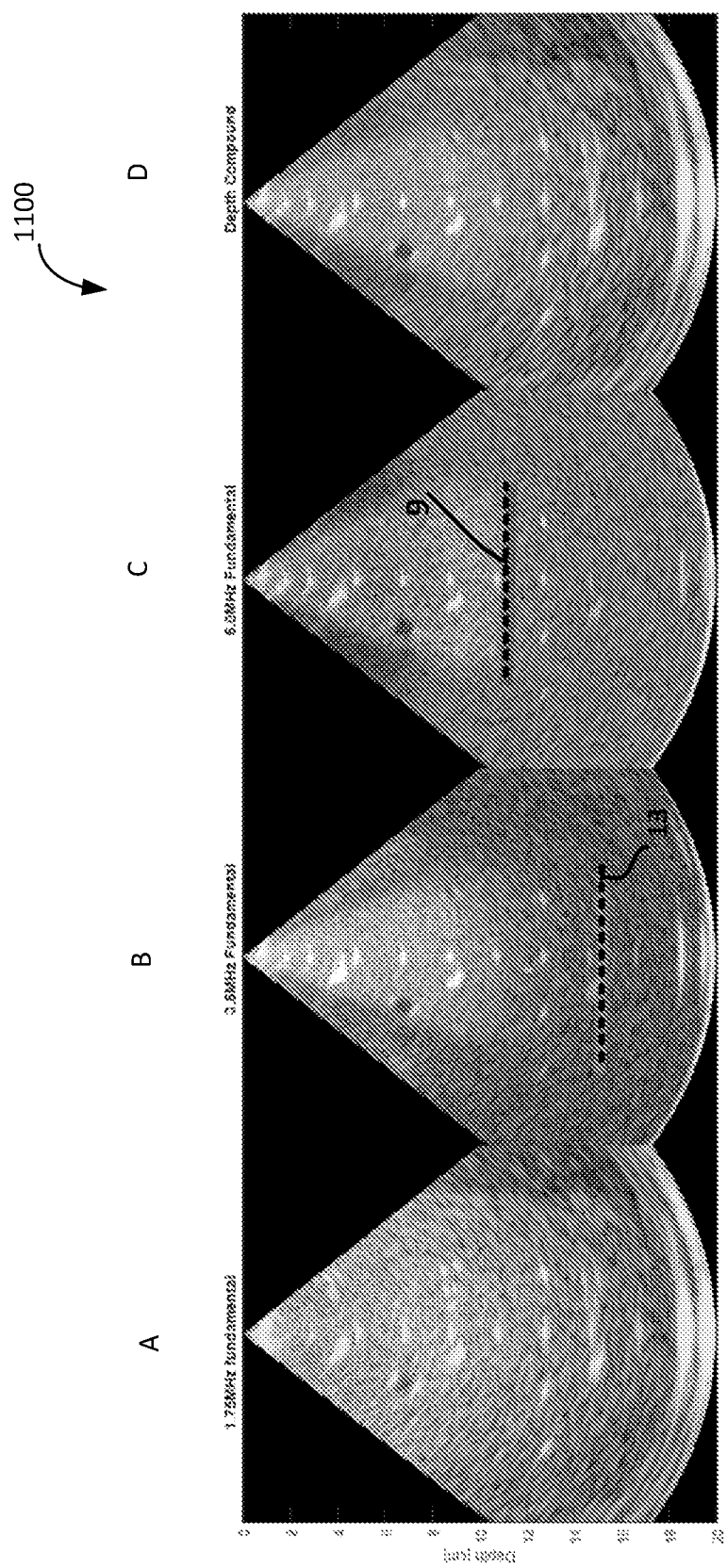
FIG. 11 is a set of images similar to those of FIG. 6, but using alpha blending with DAC with a multimodal pulse such as the one depicted in FIGS. 9A and 9B.

Some embodiments further aim to leverage the broad band of transducer elements of a transducer array, such as those described above, by effectively generating a multimodal transmitted ultrasonic waveform at a number of fundamental frequency pulses, including low and high frequency pulses, and imaging at the same or similar frequency pulses as the fundamental frequency pulses. In a multimodal imaging (MI) implementation, frequencies of the reflected ultrasonic waveform that are processes may for example be used to generate, substantially simultaneously, the respective electrical signals representative of the reflected ultrasonic waveform. FIG. 11 is a representative figure that depict THI according to some embodiments. These figures will be explained in detail further below.

Figure 5:
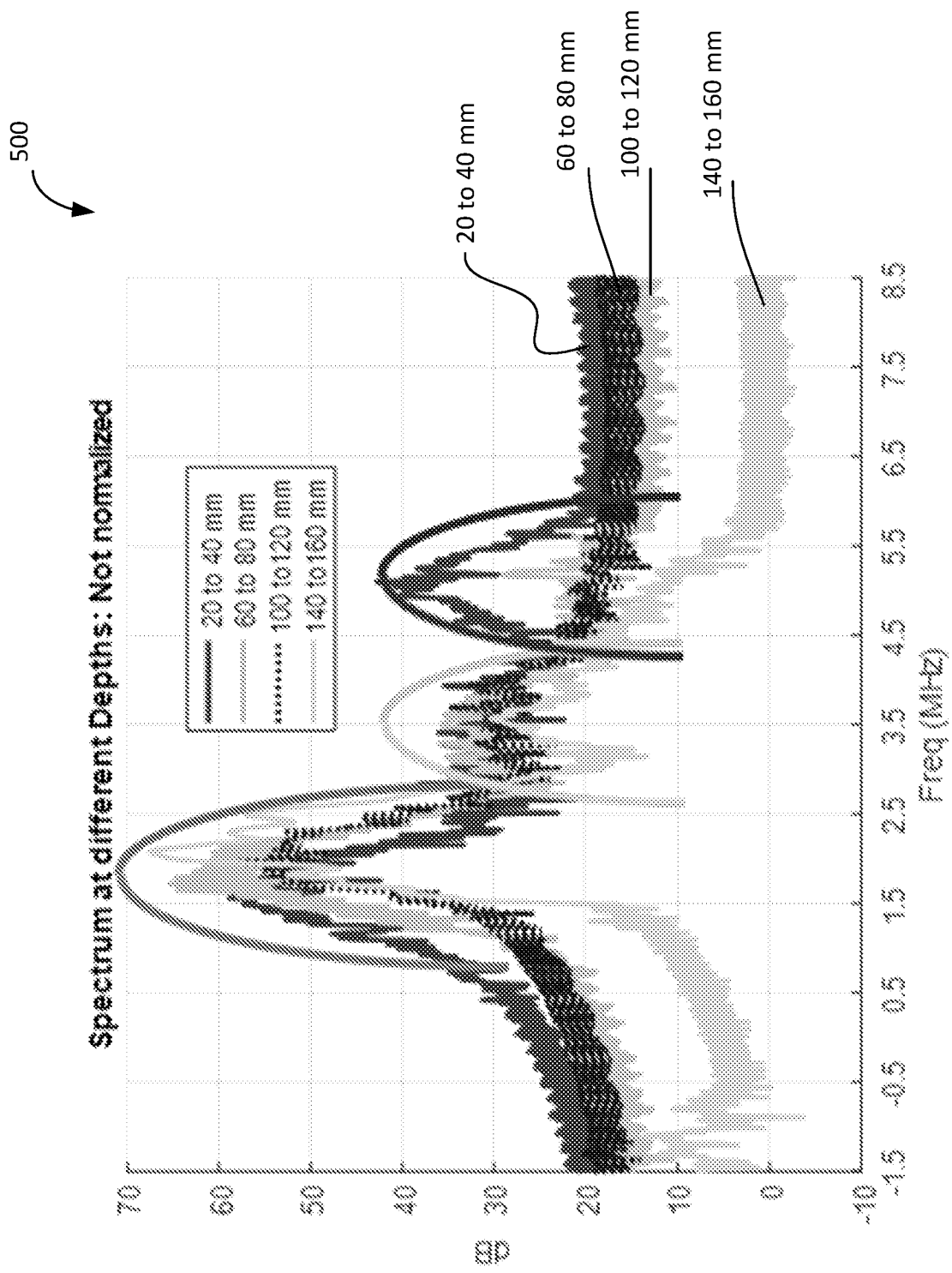
FIG. 5 is a series of graphs plotting power in Decibels (DB) versus frequency in megaHertz (MHz) for a received ultrasonic waveform at different frequencies and different penetration depths of an imaging target.

FIG. 5 is a plot 500 showing a series of graphs plotting power in Decibels (DB) versus frequency in megaHertz (MHz) for a received ultrasonic waveform at different frequencies and different penetration depths of an imaging target. As shown in FIG. 5, a reflected ultrasonic waveform may exhibit higher power at lower frequencies (1.5 MHz), and hence better penetration (noting that depth of even 140-160 mm are associated with higher DBs), while the reflected ultrasonic waveform may exhibit lower and lower power as the frequency increases. Even at shallow penetrations (e.g. 20-40 mm), the lower frequencies exhibit higher power. FIG. 5 shows the benefit of lower frequencies in terms of resolution at larger penetrations as noted above. The figure further suggests that, for shallower penetrations or depths, the higher frequencies may lead to better resolution (see e.g. the plot for the depth of 20-40 mms).

Some embodiments allow leveraging advantages of the higher harmonics (when THI is used) or higher frequencies (when MI is used), which provide higher spatial resolution overall (as compared with the lower harmonics/lower frequencies) and with the advantages of the lower harmonics/lower frequencies. The lower harmonics/lower frequencies provide better penetration resolution (as compared with the higher harmonics/higher frequencies). "Penetration" as used herein refers to imaging depth of the target object.

Some embodiments advantageously allow using a broad band of the transducer elements to extract high information content at all imaging depths from electrical signals generated from a reflected ultrasonic waveform. Some embodiments extract the high information content by: (1) processing the reflected ultrasonic waveform at a higher frequency to obtain electrical signals corresponding to the near field of an image (field that correspond to lower/shallower penetrations) and corresponding to tighter lateral image angles (with lateral image angle referring to an angle θ as will be explained in further detail in the context of FIG. 6); and (2) processing the reflected ultrasonic waveform at a lower frequency to obtain electrical signals corresponding to the far field of an image (field that corresponds to higher/deeper penetrations) and/or for wider lateral image angles.

FIGS. 6, 7, 10, 11, 12 and 13 show ultrasonic images which correspond to ultrasonic frames. A "frame" or "image" as referred to herein refers to an image of a cross-sectional plane through the object, and may be made up of individual scan lines. A scan line may be viewed as an individual layer or slice of an image. Depending on the resolution, a particular image may include different numbers of scan lines ranging from less than a hundred to many hundreds.

Reference is now made to FIG. 6, which show a set 600 of four respective ultrasonic images of a target object, with the depth having been plotted on the left axis in cm, where an output image, image D, is obtained through simple averaging of pixel irradiances of images A-C, where each of images A-C corresponds to a given reflected frequency. In FIG. 6, images A, B, C and D show, respectively: A. an image generated from electrical signals corresponding to a first frequency of the reflected ultrasonic waveform, the first frequency corresponding to the fundamental frequency of transmission of the transmitted ultrasonic waveform; B. an image generated from electrical signals corresponding to a second frequency of the reflected ultrasonic waveform, the second frequency corresponding to a second harmonic of the fundamental frequency; C. an image generated from electrical signals corresponding to a third frequency of the reflected ultrasonic waveform, the third frequency corresponding to a third harmonic of the fundamental frequency; and D. an image generated from a simple compounding of the electrical signals of respective ones of images A through C. The line 13 and line 9 in FIG. 6 show, respectively, the penetration depth at 13 cm and 9 cm.

FIG. 6 is representative of issues that may arise if one is imaging based on a single receive frequency (i.e. a single frequency at which the reflected ultrasonic waveform is to be processed or demodulated to generate the output image to be displayed). Looking at image A for example, we have better penetration resolution overall, and better resolution at wider image angles θ (with θ representing the angle of either side of line CL). However, when compared with the resolution at shallower depths for images B and C (as exhibited in images B and C by the "spotlight" regions SL), the resolution of image A at shallower depths could be improved. Thus, no one image for a given receive frequency may provide an adequate image with enough resolution at desired depths and/or image angles. In addition, it is desirable to keep the resolution while doing away with a SL region so as to have a more uniform image.

FIG. 6 highlights the fact that improvement of an image may take place in a number of dimensions, such as, along a depth of the target object as shown, and across angle θ as well. For wider angles θ, higher frequencies will not have a good fidelity or signal to noise ratio as compared with lower frequencies.

Some embodiments contemplate leveraging the better resolution obtained from electrical signals corresponding to lower frequency processing of a reflected ultrasonic waveform for both deeper penetrations and wider angles.

FIG. 6, discussed above as a figure that is representative of some of the issues that may arise with ultrasonic imaging, shows the centerline CL from which θ may be measured, and the spotlight region SL corresponding to regions of better resolution for higher frequency processing. FIGS. 7, and 10-12 show images comparable in kind to those of FIG. 6, and, as a result, the depiction of CL, SL and θ has been omitted in those pictures, although it is to be understood that the concepts of CL, SL and θ as discussed in the context of FIG. 6 are equally as applicable to FIGS. 7, and 10-12, and may be discussed below in the context of those figures.

FIGS. 6, 7, 10 and 11 show examples of THI, where a single low-frequency transmit pulse (1.75 MHz) applied to a transmitted ultrasonic waveform, and the resulting reflected ultrasonic waveform is demodulated at three imaging frequency bands (1.75 MHz, 3.5 MHz, 5.25 MHz). For THI, a narrow base-band filter may be applied for electrical signals corresponding to demodulation of the three imaging harmonics, followed by further processing to generate electrical signals corresponding to three images, namely images A, B and C for each of FIGS. 6, 7, 10 and 11. The electrical signals corresponding to the three images A-C may then be compounded according to any of the compounding processes listed below in order to improve contrast resolution, spatial resolution, or penetration resolution. Some compounding methods according to embodiments may include: simple averaging, weighted averaging, alpha blending with depth adaptive compounding, gain-compensated compounding, maximum and minimum adaptive compounding, predictive compounding, lateral frequency adaptive compounding and Doppler compounding. Such compounding methods will be described in further detail below.

Simple Averaging

Reference is made again to FIG. 6, which has already been described in part above. According to the example of FIG. 6, compounding of electrical signals corresponding to the images of three receive frequencies (in the case of FIG. 6, the fundamental and two harmonics—although simple averaging according to embodiments may be used in the multimodal imaging embodiment as well) at A, B and C may be achieved by way of simple averaging to obtain the image at D. Simple averaging in the context of FIG. 6 may involve, for each given pixel location defined by a depth and an image angle, averaging respective pixel irradiances of said given pixel location corresponding to respective ones of the receive frequencies.

For a given frequency of a reflected ultrasonic waveform, "pixel irradiance" I at a given pixel location refers to the flux of radiant energy per unit area (normal to the direction of flow of radiant energy) at the given pixel location that would be generated based on electrical signals corresponding to the given receive frequency.

For example, pixel irradiances at each of the receive frequencies for a given pixel location, say at a depth of 8 cm and an image angle of 5 degrees, may be used to compute a simple averaging of the pixel irradiance at that location, and used to generate the pixel irradiance at image D. The latter would be a linear average. Reference is made to Equation 1 below for simple averaging:

$$I_{out}=(I_{high}+I_{mid}+I_{low})/3 \qquad \text{Eq. (1)}$$

where:

$I_{out}$ is the output pixel irradiance at a given pixel location for the output image (image D);

$I_{high}$ is the pixel irradiance at the given pixel location for the high receive frequency image (image C);

$I_{mid}$ is the pixel irradiance at the given pixel location for the middle receive frequency image (image B); and $I_{low}$ is the pixel irradiance at the given pixel location for the low receive frequency image (image A).

Weighted Averaging

With compounding involving weighted averaging, the pixel irradiance at a given pixel location may be obtained through an equation such as Equation 2 below:

$$I_{out}=(\alpha \times I_{high}+\beta \times I_{mid}+\gamma \times I_{low})^3 \qquad \text{Eq. (2)}$$

where $I_{out}$, $I_{high}$, $I_{mid}$ and $I_{low}$ are as defined for Equation 1 above, and where α, β and γ are weights to be used for each of the noted pixel irradiances. α, β and γ may be based on application needs, such as whether depth resolution is needed.

Alpha-Blending Urine Depth Adaptive Compounding

Figure 8:
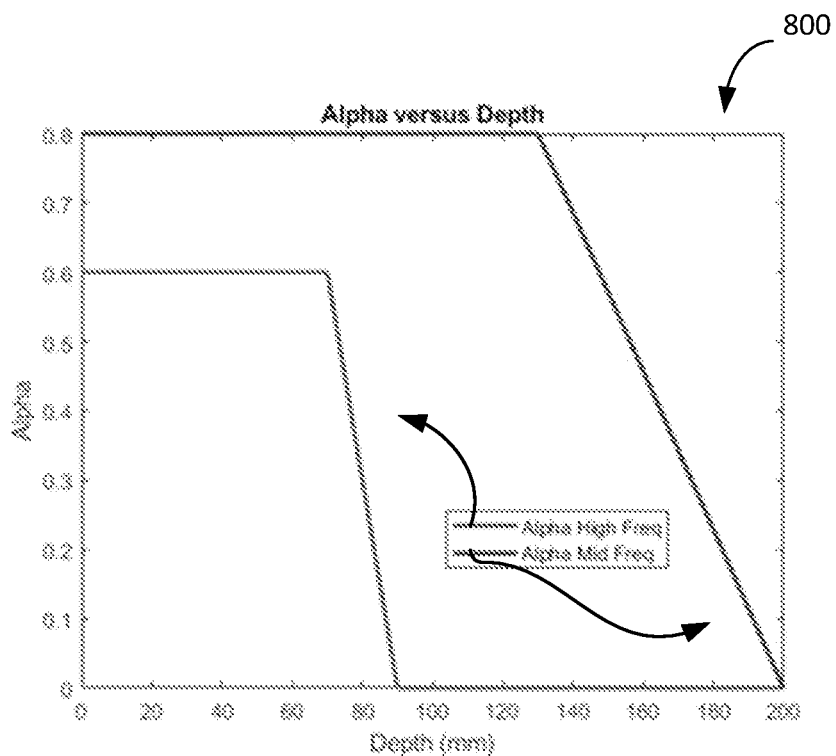
FIG. 8 is an example of a plot of a value versus depth for the alpha blending using DAC.

Reference is now made to FIGS. 7 and 8 in the context of a compounding method according to one embodiment which involves alpha blending using depth adaptive compounding (DAC).

FIG. 7 shows a set 700 of four respective ultrasonic images of a target object, where an output image, image D, is obtained through alpha blending DAC of pixel irradiances of images A-C. Images A-C of FIG. 7, similar to those in FIG. 6, correspond to: an image obtained at a receive frequency that is equal to the fundamental frequency (A), an image obtained at a receive frequency equal to the second harmonic of the fundamental frequency (B), and an image obtained at a receive frequency equal to the third harmonic of the fundamental frequency (C). Line 13 shows the penetration depth at 13 cm, and line 9 shows the penetration depth at 9 cm.

Alpha blending using DAC in the context of FIG. 7 may involve, for each given pixel location defined by a depth and an image angle, multiplying respective pixel irradiances of said given pixel location corresponding to respective ones of the receive frequencies by a respective alpha multiplier. Each of the multipliers for each of the pixel irradiances at a given pixel location may be a function of one or more alpha values, where individual alpha values are a function of penetration depth.

Reference is made to Equation 3 below for an example of alpha blending using DAC:

$$I_{out}=I_{high} \cdot \alpha_{high}+(1-\alpha_{high}) \cdot (\alpha_{mid} \cdot I_{mid}+(1-\alpha_{mid}) \cdot I_{low}) \quad \text{Eq. (3)}$$

where $I_{out}$, $I_{high}$, $I_{mid}$ and $I_{low}$ are as defined for Equation 1 above, and where:

$\alpha_{high}$ corresponds to a depth dependent a value of the high receive frequency; and $\alpha_{mid}$ corresponds to a depth dependent a value of the middle receive frequency.

Thus, the multiplier for each of the pixel irradiances from Equation 3 above may be as follows:

$\alpha_{high}$: $I_{high}$ multiplier;
$(1-\alpha_{high}) \times \alpha_{mid}$: $I_{mid}$ multiplier; and
$(1-\alpha_{high}) \times (1-\alpha_{mid})$: $I_{low}$ multiplier FIG. 8 is one example of a plot 800 of a value versus depth in mm for $\alpha_{high}$ and $\alpha_{mid}$, which are used in Equation 4 above. It is clear from plot 800 that a value for $\alpha_{high}$ may drop to zero at a given depth, such as, in the case of the example of plot 800, at a depth of about 92 mm. In contrast, the a value of $\alpha_{mid}$ drops to zero much more gradually than $\alpha_{high}$, and drops to zero at a much deeper penetration, in the case of the example of plot 800, at 200 mm. Alpha blending using DAC therefore may aim to minimize the contribution of the higher receive frequencies to pixel irradiance at deeper depths, given the low resolution and fidelity. For deeper pixel locations, the contribution of the pixel irradiances at the high and middle receive frequencies may go to zero, in which case alpha blending with DAC would use only the pixel irradiance of the lower receive frequency (in the case of FIG. 8, above 200 mm).

Thus, the multipliers of the pixel irradiances for various receive frequencies may be based on a depth of the pixel location Multimodal Transmitted Ultrasonic Waveforms As noted above embodiments, and hence the compounding methods described herein, do not require that the transmitted ultrasonic waveform have a single fundamental frequency as the transmit frequency, with the received frequencies of the reflected ultrasonic waveform including harmonics of that fundamental frequency (THI). Some other embodiments include within their scope the use of a transmitted ultrasonic waveform that is characterized by three fundamental frequencies as the transmit frequencies, with the received frequencies corresponding to the fundamental frequencies (MI). As noted above, some transducer elements may have multimodal capability, and may thus correspond to multi-modal elements, which would make the multimodal imaging modality possible. Embodiments encompass within their scope a computing device which is capable of processing electrical signals based on both the THI modality and the MI modality.

Figures 9A, 9B:
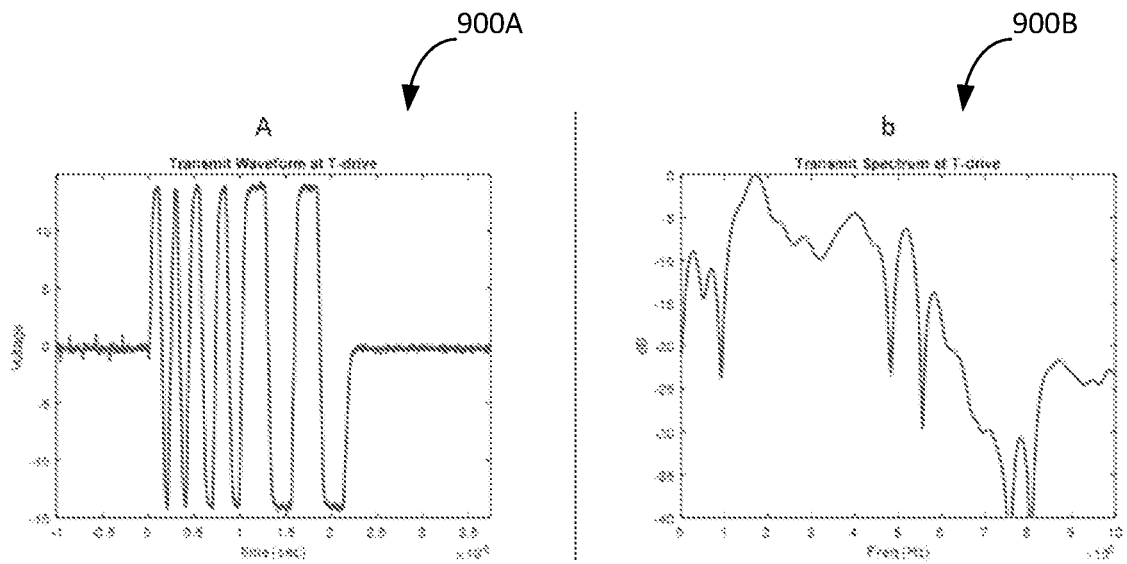
FIG. 9A shows a plot of voltage against time in seconds for a multimodal pulse using fundamental frequencies for transmit with pulses 1.75 MHz, 3.5 MHz and 5.1 MHz.
FIG. 9B shows a plot of a frequency distribution for the transmitted ultrasonic waveform of FIG. 9A, plotting power in DB versus frequency in Hz.

FIGS. 9A, 9B, 10 and 11 relate to the use of MI for better penetration resolution, and show an example multimodal pulse which may be used in the MI embodiment described herein. In particular, FIG. 9A shows a plot 900A showing voltage plotted against time in seconds for a multimodal pulse using fundamental frequencies for transmit with pulses 1.75 MHz, 3.5 MHz and 5.1 MHz. FIG. 9B shows a plot 900B of a frequency distribution for the transmitted ultrasonic waveform of FIG. 9A, plotting power in DB versus frequency in Hz.

FIG. 10 is a set 1000 of images similar to those of FIG. 6, but this time using the pulse of FIGS. 9A and 9B to generate the images A-C, and further using simple compounding as explained above to compound electrical signals correspond to images A-C in order to generate the compound image D.

FIG. 11 is a set 1000 of images similar to those of FIG. 6, but using alpha blending with DAC as explained above, on a multimodal pulse such as the one depicted in FIGS. 9A and 9B.

As can be seen from a comparison of FIGS. 11 and 10, alpha blending with DAC in MI in the shown example results in an output image D with better resolution overall as compared with simple compounding in MI. As can be seen from a comparison of FIGS. 6 and 10, simple compounding in THI in the shown example results in an output image D with better overall resolution as compared with simple compounding in MI. As can be seen from a comparison of FIGS. 7 and 11, alpha blending with DAC in THI in the shown example results in an output image D with better overall resolution as compared with adaptive compounding in MI. As can be seen from a comparison of FIGS. 11 and 6, alpha blending with DAC in MI in the shown example results in an output image D with better overall resolution as compared with adaptive compounding in THI.

Gain-Compensated Before Compounding

According to one embodiment a compounding method may including gain-compensated compounding, according to which the individual frequency bands of the reflected ultrasonic waveform may be pre-processed prior to compounding. For example, the electrical signals corresponding to each of the receive frequencies being processed for image generation may be subjected to gain compensation or dynamic range (DR) compensation to improve the quality of the output image.

Figure 12:
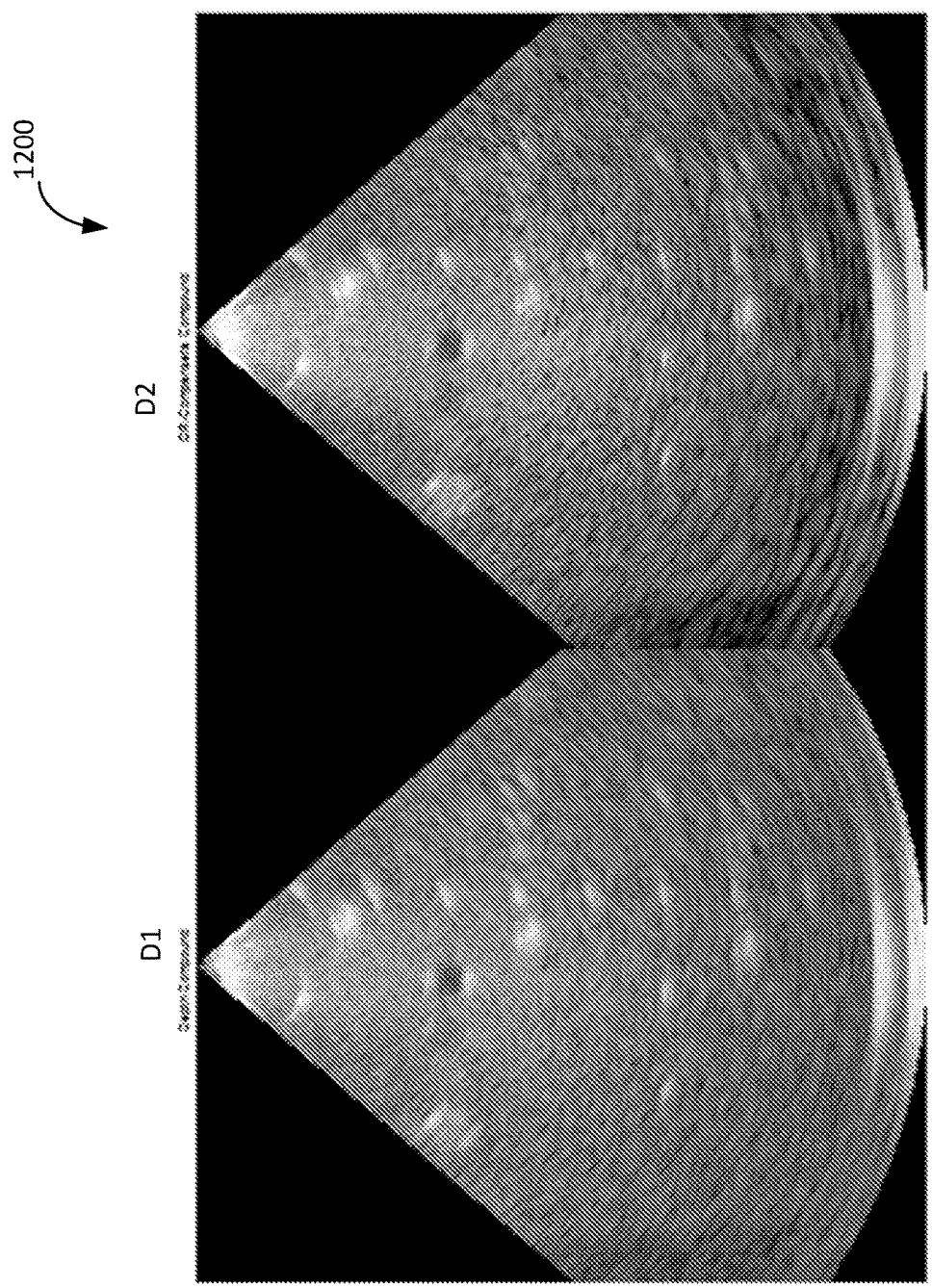
FIG. 12 shows two output images D1 and D2, with image D1 representing one obtained using alpha blending with DAC on three receive frequencies similar to those of FIG. 6, and with D2 representing one obtained using DR compensation on the same three receive frequencies.

Reference is now made to FIG. 12, which shows two output images D1 and D2, with image D1 representing one obtained using alpha blending with DAC on three receive frequencies similar to those of FIG. 6, 7, 10 or 11, and with D2 representing one obtained using DR compensation on the same three receive frequencies, with a DR of 60 and different gains. A comparison of D1 and D2 shows the clear benefit of improved contrast using DR compensation as compared with alpha blending using DAC, all else being equal.

Maximum and Minimum Adaptive Compounding

Adaptive compounding in general involves several non-linear methods of combining or compounding electrical signals corresponding to receive frequencies of reflected ultrasonic waveforms. An example adaptive compounding technique will be described below.

Figure 13:
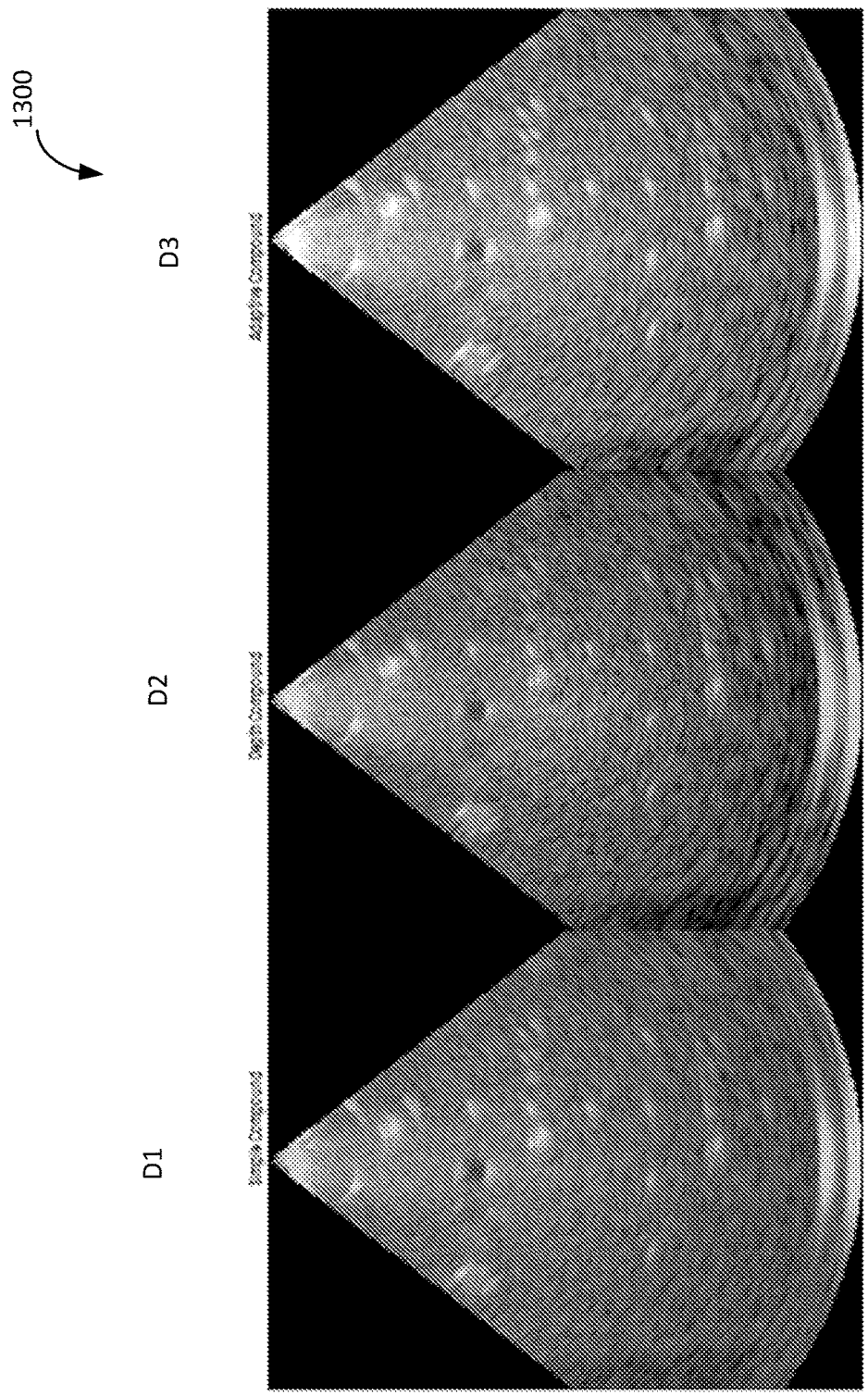
FIG. 13 shows a set of three output images D1, D2 and D3, with image D1 representing one obtained using simple compounding on three receive frequencies similar to those of FIG. 6, with D2 representing one obtained using alpha blending with DAC on the same three receive frequencies, and with D3 representing one obtained using adaptive compounding.

Reference is now made to FIG. 13, which shows a set of three output images D1, D2 and D3, with image D1 representing one obtained using simple compounding on three receive frequencies similar to those of FIG. 6, 7, 10 or 11, with D2 representing one obtained using alpha blending with DAC on the same three receive frequencies, and with D3 representing one obtained using maximum and minimum adaptive compounding according to Equation 5 below. A comparison of D1, D2 and D3 shows the clear benefit of improved contrast and better resolution using adaptive compounding as compared with simple compounding and alpha blending using DAC, all else being equal.

Output image D3 of FIG. 13 is a result of a simple non-linear adaptive compounding method that uses a blend of the maximum, minimum and mean frames or pixel irradiances according to Equation 4 below:

$$I_{out}=I_{max} \cdot \alpha_{max}+(1-\alpha_{max}) \cdot (\alpha_{min} * I_{min}+(1-\alpha_{min}) \cdot I_{depth\_comp}) \quad \text{(Eq. 4)}$$

where:

$I_{max}$: MAX ($I_{high}, I_{mid}, I_{low}$);

$I_{min}$: MIN ($I_{high}, I_{mid}, I_{low}$);

$I_{depth\_comp}$ corresponds to pixel irradiance at the pixel location after alpha blending with depth compensation as explained above in the context of Equation 3;

$\alpha_{max}$: a maximum transparency coefficient ("alpha value," or a transparency coefficient to be used on $I_{max}$) based on known alpha blending methods. For example, $\alpha_{max}$ may be determined from a lookup table that maps irradiance (i.e. at least one of $I_{max}, I_{min},$ or $I_{depth\_comp}$) to a given value, such as, for example, between and including 0 and 1. Thus, according to one example, where an irradiance chosen (i.e. the at least one of $I_{max}, I_{min},$ or $I_{depth\_comp}$) is greater than a threshold X1, then $\alpha_{max}$ may have a set first value (e.g. between and including 0 and 1); when the irradiance chosen is less than X2, $\alpha_{max}$ may have a second set value (between and including 0 and 1, where the second set value is different from first set value); when the irradiance chosen is between X1 and X2, $\alpha_{max}$ is determined based on a linear function, a straight line between the first set value and the second set value; and $\alpha_{min}$: a minimum transparency coefficient (a transparency coefficient to be used on $I_{max}$) based on known alpha blending methods. For example, similar to $\alpha_{max}$, $\alpha_{min}$ may be determined from a lookup table that maps irradiance (i.e. at least one of $I_{max}, I_{min},$ or $I_{depth\_comp}$) to a given value, such as, for example, between and including 0 and 1. Thus, according to one example, where an irradiance chosen (i.e. at least one of $I_{max}, I_{min},$ or $I_{depth\_comp}$) is greater than a threshold X1, then $\alpha_{min}$ may have a set first value (e.g. between and including 0 and 1); when the irradiance chosen is greater than X2, $\alpha_{min}$ may have a second set value (between and including 0 and 1, where the second set value is different from first set value); when the irradiance chosen is between X1 and X2, $\alpha_{min}$ may be determined based on a linear function, a straight line between the first set value and the second set value.

Predictive Compounding

Predictive compounding according to some embodiments involve a determination of the relationship between first electrical signals corresponding to a first region (region NF) of an image based on a first receive frequency, and electrical signals corresponding to the first region (region NF) of an image based on a second receive frequency, and predicting third electrical signals corresponding to a second region (region FF) of an image based on the second receive frequency. For example, referring to FIG. 6, predictive compounding may be used to determine the relationship between the electrical signals corresponding to region NF1 (region NF of the 1.75 MHz receive frequency) and the electrical signals corresponding to regions A2 (region NF of the 3.5 MHz receive frequency). Predictive compounding may then include using the relationship, along with the electrical signals at region FF1 (region FF of the 1.75 MHz receive frequency) to predict the electrical signals at region FF2 (region FF of the 3.5 MHz receive frequency).

The relationship may for example be helpful in allowing one to use the better penetration of lower frequencies as input signals to predict images at deeper penetrations at the higher receive frequencies. Thus, we can replace the images at the deeper depths of the target object at higher frequencies with images predicted from the same depths at the lower frequencies.

Some examples of predictive compounding are described below, including simple predictive compounding, predictive compounding using points spread functions (PSFs), and machine learning (ML)-based predictive compounding.

Simple Predictive Compounding

A simple method to use predictive compounding may involve the use of Equation 5:

$$I_{FF2} = I_{FF1} \cdot I_{NF2}/I_{NF1} \quad \text{Eq. (5)}$$

where:

$I_{FF2}$: pixel irradiance at region FF2—this is the predicted pixel irradiance;

$I_{FF1}$: pixel irradiance at region FF1, obtained from the reflected ultrasonic waveform;

$I_{NF2}$: pixel irradiance at region NF2, obtained from the reflected ultrasonic waveform; and $I_{NF1}$: pixel irradiance at region NF1, obtained from the reflected ultrasonic waveform.

The reverse can be done as well, where a higher resolution region from the higher receive frequencies may be used to predict a same region for the lower receive frequencies. The lower receive frequencies do not have as good of a resolution as the higher receive frequencies. Using adaptive predictive compounding will let us use the better resolution of the higher frequency with the benefits of the lower penetration of lower frequency image, thus resulting in an image with some predicted portions that for example show better penetration at the higher frequencies.

By way of example, once a relationship is found as explained above, for a 5 MHz image with predictive compounding, there can be, for instance, a 10× better penetration than with a 5 MHz image without predictive compounding.

Predictive Compounding Using Point Spread Functions (PSF)

The point spread function (PSF) of a reflected ultrasonic waveform depends on a number of factors, including receive frequency, receive bandwidth, and focus at the target object. The PSF may be thought of as representing a scattering of the reflected beam from the target object. To obtain the image corresponding to the region of the target object being imaged, as a predictive measure, PSF may be convolved with the scattering distribution corresponding to the region of the target object being imaged, such as a pixel. Thus, the frequency dependent PSF may be convolved with the target object dependent scattering distribution. Therefore, when the received frequency is different, say, when we are going from a receive frequency of 1.75 MHz up to 3.5 MHz, the PSF would change, but the scattering distribution would be the same for a same region being imaged.

Let us suppose, as noted above in the general discussion of predictive compounding for example in the context of the images of FIG. 6, that:

region NF1 corresponds to region NF of the 1.75 MHz receive frequency image;

region FF1 corresponds to region FF of the 1.75 MHz receive frequency image;

region NF2 corresponds to region NF but of the 3.5 MHz receive frequency image;

region FF2 corresponds to region FF but of the 3.5 MHz receive frequency image;

PSF1 corresponds to PSF for the 1.75 MHz receive frequency image;

PSF2 corresponds to PSF for the 3.5 MHz receive frequency image; and

PSFinverse is an inverse of the PSF.

Given the above definitions, we can assume that, if we want to predict the pixel irradiance at B2, representative of the scattering distribution (which correlates with the target object at region FF), we can use Equation 6:

$$I_{FF2} = I_{NF2} \times (I_{FF1} * PSF2_{inverse})/(I_{NF1} * PSF1_{inverse})$$ Eq. (6)

where $*PSF_{inverse}$ denotes a deconvolution based on PSF.

ML-Based Predictive Compounding

Some embodiments propose a ML-based prediction compounding which may use a ML-based deconvolution to provide a higher resolution image (e.g. 5 MHz) in the far-field while preserving the penetration of the lower frequency (e.g. 1.75 MHz).

Proposed Method:

The basic idea is a) identify a relationship between the local regions of the low frequency and high-frequency image using the near-field data and b) obtain a high-frequency image in the far-field by applying the identified relationship on the low-frequency image. The steps below detail the proposed method.

Training and Validation DataSet:

The following operations may be performed to carry out a ML-based compounding according to some embodiments:
1) choosing the 1.75 MHz image as the input and the 5.0 Mhz as the desired output image;
2) choosing a near-field region NF (e.g. at a depth of 0-5 cm) in each of the 1.75 MHz and 5.0 MHz images;
3) segmenting the near-field region NF into many "speckle cells" to create a training data set, that is, to create many subregions, for example square subregions measuring 5 mm×5 mm, within both the near-field region to create inputs (1.75 MHz subregions) and the outputs (5.0 Mhz subregions);
4) using multiple frames and/or multiple views of individual subregions to create the training data set; for instance, using about 50 different imaging views on a pin target phantom and on a speckle phantom of each subregion could create about 5000+ images to use as the training data set, which could, optionally, also be augmented by translation, scaling etc. if necessary;
5) use mid-field speckle cells at a (5-10 cm) to create the validation dataset.
6) using a midfield region MF (e.g. at a depth of 0-5 cm) in each of the 1.75 MHz and 5.0 MHz images as a validation dataset;
7) developing a ML-based training model for the relationship between regions A of the 1.75 MHz and the 5 MHz receive frequencies based on the training data set and the validation data set; and
8) predicting an image at regions B of the 1.75 MHz and the 5 MHz receive frequencies based on the training model, wherein B is the far field region.

The training data set can be used identify the relationship between regions A as between the lower and higher receive frequencies. This relationship may also be used for other ML-related applications, such as identifying a speckle cell, differentiating speckle from noise, gain equalization, edge enhancement, etc.

Lateral Frequency Compounding

Reference is again made to FIG. 6 as being representative of issues that may arise if one is imaging based on a single receive frequency. Looking at image A for example, we have better penetration resolution overall, and better resolution at wider image angles θ (with θ representing the angle of either side of line CL). Images B and C however show a spotlight region SL in the near field and midfield regions. The SL is missing from the lower frequency image A however.

Lateral frequency compounding may involve, for each given pixel location defined by a depth and an image angle, multiplying respective pixel irradiances of said given pixel location corresponding to respective ones of the receive frequencies by a respective alpha multiplier. Each of the multipliers for each of the pixel irradiances at a given pixel location may be a function of one or more alpha values, where individual alpha values may be a function of both image angle and penetration depth.

Reference is made to Equation 7 below for an example of lateral frequency compounding:

$$I_{out}(r,\theta) = I_{high} \cdot \alpha_{high}(r,\theta) + (1 - \alpha_{high}(r,\theta)) \cdot \\ (\alpha_{mid}(r,\theta) * I_{mid} + (1 - \alpha_{mid}(r,\theta)) \cdot I_{low})$$ Eq. (7)

where:
$I_{out}(r,\theta)$: output pixel irradiance at depth r and at image angle θ;
$I_{high}$: pixel irradiance at depth r and at image angle θ for the high receive frequency image (image C);
r: image depth;
θ: image angle;
$\alpha_{high}(r,\theta)$: transparency coefficient α at depth r and at image angle θ for the high receive frequency, where $\alpha_{high}(r,\theta)$ may be determined in the same manner as explained above for either of $\alpha_{max}$ or $\alpha_{min}$, with a difference being that $\alpha_{high}(r,\theta)$ can have different ranges and different break points X1 and X2 for different r's and different θ's;
$\alpha_{mid}(r,\theta)$: transparency coefficient α at depth r and at image angle θ for the middle receive frequency, where $\alpha_{mid}(r,\theta)$ may be determined in the same manner as explained above for either of $\alpha_{max}$ or $\alpha_{min}$, with a difference being that $\alpha_{mid}(r,\theta)$ can have different ranges and different break points X1 and X2 for different r's and different θ's;
$I_{mid}$: the pixel irradiance at depth r and at image angle θ for the middle receive frequency image (image B);
$I_{low}$: the pixel irradiance at depth r and at image angle θ for the low receive frequency image (image A).

Thus, the multiplier for each of the pixel irradiances from Equation 4 above may be as follows:
$\alpha_{high}(r,\theta)$: $I_{high}$ multiplier;
$(1 - \alpha_{high}(r,\theta)) \cdot (\alpha_{mid}(r,\theta))$: $I_{mid}$ multiplier; and
$(1 - \alpha_{high}(r,\theta)) \cdot (1 - \alpha_{mid}(r,\theta))$: $I_{low}$ multiplier.

The coefficient α (transparency coefficient) is thus a function of image angle to reduce the "spot-light" artefacts in the higher frequencies, as well as improve the signal to noise ratio (SNR) in the lateral directions. Equation 9 below depicts the above relationship:

$$\text{Img}_{out}(r,p) = \Sigma_{i=1}^{3} \alpha(r,p,i) \cdot \text{Img}_{in}(r,p,i)$$ Eq. (8)

where:
i: frequency band of imaging waveforms;
p: line index coordinate for the image;
$\text{Img}_{out}(r, p)$: output image irradiance at depth r and line index coordinate p;
$\text{Img}_{in}(r, p, i)$: input image intensities, respectively; and
α(r, p, i): transparency coefficient for depth r, line index coordinate p, and frequency band I, where α(r, p, i) may be determined in the same manner as explained above for either of $\alpha_{max}$ or $\alpha_{min}$, with a difference being that α(r, p, i) can have different ranges and different break points X1 and X2 for different r's, different p's, and different i's.

Lateral compounding may improve the directivity and provide a larger field of views like, such as a 150 degrees field of view.

Color Doppler/Flow Compounding

Compounding using color Doppler according to some embodiments makes use of additional parameters associated with Doppler imaging, including velocity (flow and direction) in addition to irradiance. Color Doppler compounding according to some embodiments may involve combining flow velocity or power from multiple frequency data. The power or velocity from the multiple frequency bands are combined based on a) depth, b) angle, c) SNR, d) flow velocity etc.

Equations 9 through 12 may be used to calculate alpha-blended results for an output image generated using color Doppler compounding, according to one embodiment:

Max Parameter:

$$R0_{out.max} = \max(_{i=1}^{Nfreq} R0_{in}(i)) \quad \text{Eq. (9)}$$

$$R1_{out.max} = maxfreq(_{i=1}^{Nfreq} \tan^{-1}(R1_{in}(i))) \quad \text{Eq. (10)}$$

Mean Parameter:

$$R0_{out.mean} = \max\left(\sum_{i=1}^{Nfreq} R0_{in}(i)\right) \quad \text{Eq. (11)}$$

$$R1_{out.mean} = \max\left(\sum_{i=1}^{Npfreq} R1_{in}(i)\right) \quad \text{Eq. (12)}$$

where:
$R0_{out.max}$: the maximum zero lag output value of the autocorrelation corresponding to the alpha-blending to be used;
$R1_{out.max}$: the maximum first lag output value of the autocorrelation;
$R0_{out.mean}$: the mean zero lag output value of the autocorrelation corresponding to the alpha-blending to be used;
$R1_{out.mean}$: the mean first lag output value of the autocorrelation;
$R0_{in}(i)$: the zero lag input value corresponding to the frequency band i of imaging waveforms for the autocorrelation corresponding to the alpha-blending to be used (see e.g. Equations 14 and 15 below); and
$R1_{in}(i)$: the first lag input value corresponding to the frequency band i of imaging waveforms for the autocorrelation corresponding to the alpha-blending to be used (see e.g. Equations 14 and 15 below).

The maximum and mean of R0 and R1 is computed from Equations 9-12 above, and then alpha-blended as shown below in Equations 14 and 15:

$$R0_{out} = \alpha.R0_{out.max} + (1-\alpha).R0_{out.mean} \quad \text{Eq. (13)}$$

$$R1_{out} = \alpha.R1_{out.max} + (1-\alpha).R1_{out.mean} \quad \text{Eq. (14)}$$

where:
$R0_{out}$: zero lag output corresponding to an alpha blended value of the max and mean zero lag autocorrelations;
$R1_{out}$: first lag output corresponding to an alpha blended value of the max and mean first lag autocorrelations;
α: alpha value for the alpha blending.

Although the above description of exemplary embodiments may specifically mention veins, embodiments are not so limited, and pertain to the detection and tracking of any vessels with a body that may be the subject of ultrasonic imaging where the vessel is to be accessed by a foreign object. In addition, although certain colors are mentioned above to indicate suitability for access or other parameters relating to a vessel, embodiments are not so limited, and include within their scope an indication of vessel parameters to a user through a UI in any manner, such as through text, visual images or codes, voice communication.

In an example, instructions implemented by processor 326 may be provided via the memory 336 or any other memory or storage device of the imaging device, or the processor 326 or any other processor of the imaging device, may be embodied as a tangible, non-transitory, machine-readable medium including code to direct the processor 326 to perform electronic operations in the casing, such as operations corresponding to any one of the methods/processes herein. The processor 326 may access the non-transitory, machine-readable medium over the an interconnect between memory 336 and processor 326. For instance, the non-transitory, machine-readable medium may be embodied by memory 336 or a separate memory within processor 326, or may include specific storage units such as optical disks, flash drives, or any number of other hardware devices that may be plugged into the casing. The non-transitory, machine-readable medium may include instructions to direct the processor 326 to perform a specific sequence or flow of actions, for example, as described with respect to the flowchart(s) and block diagram(s) of operations and functionality depicted herein. As used herein, the terms "machine-readable medium" and "computer-readable medium" are interchangeable.

FIG. 14 illustrates a method 1400 to be performed at a computing device comprising a memory, and one or more processors coupled to the memory. Method 1400 at operation 1402 includes receiving, simultaneously, electrical signals based on respective reflected frequencies of a reflected ultrasonic waveform reflected from a target object as a result of a transmitted ultrasonic waveform. The method at operation 1404 includes compounding information from the electrical signals to generate compounded electrical signals. The method at operation 1406 includes causing generation of an output image on a display device based on the compounded electrical signals.

Any of the below-described examples may be combined with any other example (or combination of examples), unless explicitly stated otherwise. Aspects described herein can also implement a hierarchical application of the scheme for example, by introducing a hierarchical prioritization of usage for different functions (e.g., low/medium/high priority, etc.).

Although implementations have been described with reference to specific exemplary aspects, it will be evident that various modifications and changes may be made to these aspects without departing from the broader scope of the present disclosure. Many of the arrangements and processes described herein can be used in combination or in parallel implementations. Accordingly, the specification and drawings are to be regarded in an illustrative rather than a restrictive sense. The accompanying drawings that form a part hereof show, by way of illustration, and not of limitation, specific aspects in which the subject matter may be practiced. The aspects illustrated are described in sufficient detail to enable those skilled in the art to practice the teachings disclosed herein. Other aspects may be utilized and derived therefrom, such that structural and logical substitutions and changes may be made without departing from the scope of this disclosure. This Detailed Description, therefore, is not to be taken in a limiting sense, and the scope of various aspects is defined only by the appended claims, along with the full range of equivalents to which such claims are entitled.

Such aspects of the inventive subject matter may be referred to herein, individually and/or collectively, merely for convenience and without intending to voluntarily limit the scope of this application to any single aspect or inventive concept if more than one is in fact disclosed.

While preferred embodiments of the present disclosure have been shown and described herein, it will be obvious to those skilled in the art that such embodiments are provided by way of example only. It is not intended that embodiments be limited by the specific examples provided within the specification. While embodiments of the disclosure have been described with reference to the aforementioned specification, the descriptions and illustrations of the embodiments herein are not meant to be construed in a limiting sense. Numerous variations, changes, and substitutions will now occur to those skilled in the art without departing from the concepts of the present disclosure. Furthermore, it shall be understood that all aspects of the various embodiments are not limited to the specific depictions, configurations, or relative proportions set forth herein, which depend upon a variety of conditions and variables. It should be understood that various alternatives to the embodiments described herein may be employed. It is therefore contemplated that the disclosure also covers any such alternatives, modifications, variations or equivalents.

Examples

Illustrative examples of the technologies disclosed herein are provided below. An embodiment of the technologies may include any one or more, and any combination of, the examples described below.

Example 1 includes an apparatus of a computing device comprising a memory, and one or more processors coupled to the memory to: receive, simultaneously, electrical signals based on respective reflected frequencies of a reflected ultrasonic waveform reflected from a target object as a result of a transmitted ultrasonic waveform; compound information from the electrical signals to generate compounded electrical signals; and cause generation of an output image on a display based on the compounded electrical signals.

Example 2 includes the subject matter of Example 1, wherein the respective reflected frequencies correspond to respective harmonics of a fundamental frequency of the transmitted ultrasonic waveform, the fundamental frequency being a single frequency of the transmitted ultrasonic waveform.

Example 3 includes the subject matter of Example 1, wherein the transmitted ultrasonic waveform is a multimodal waveform with fundamental frequencies that correspond to the respective frequencies of the reflected ultrasonic waveform.

Example 4 includes the subject matter of Example 1, wherein the one or more processors are to compound the information by: implementing a predictive algorithm on the electrical signals, the one or more processors to use information from first electrical signals corresponding to a first image region of the target object to generate predictive electrical signals for a second image region of the target object different from the first image region; and using the predictive electrical signals to obtain the compounded electrical signals such that the output image at the second image region corresponds to the predictive electrical signals.

Example 5 includes the subject matter of any one of Examples 1-4, wherein: the reflected frequencies include N reflected frequencies; the electrical signals include N sets of electrical signals, with each set of electrical signals corresponds to one of the reflected frequencies, the N sets of electrical signals corresponding to N input images of the target object; individual input images include pixels at respective pixel locations, with each pixel location of the N input images being defined by a depth and an angle; compounding information includes compounding information from the N sets of electrical signals; and the one or more processors are to compound the information from the N sets of electrical signals by using at least one of simple averaging, weighted averaging, alpha blending with depth adaptive compounding, maximum and minimum adaptive compounding, predictive compounding, lateral frequency compounding and color Doppler compounding.

Example 6 includes the subject matter of Example 5, where the one or more processors are further to subject the electrical signals to gain compensation or dynamic range compensation prior to compounding.

Example 7 includes the subject matter of Example 5, wherein simple averaging includes, for each pixel location, performing one of a simple averaging or a weighted averaging of respective pixel irradiances across the N input images.

Example 8 includes the subject matter of Example 5, wherein alpha blending with depth adaptive compounding includes, for each pixel location, multiplying, by a corresponding alpha multiplier, respective pixel irradiances as between the N input images, each alpha multiplier a function of one or more alpha values, the one or more alpha values a function of at least one of depth of said each pixel location or angle of said each pixel location.

Example 9 includes the subject matter of Example 8, wherein, for said each pixel location, an output irradiance at the output image is given by: $I_{out}=I_{high} \cdot \alpha_{high}+(1-\alpha_{high}) \cdot (\alpha_{mid} \cdot I_{mid}+(1-\alpha_{mid}) \cdot I_{low})$ where: $I_{out}$ is an output pixel irradiance for said each pixel location for the output image; $I_{high}$ is a pixel irradiance for said each pixel location for an input image corresponding to a highest one of the received frequencies; $I_{mid}$ is a pixel irradiance for said each pixel location for an input image corresponding to a middle one of the received frequencies; $I_{low}$ is a pixel irradiance for said each pixel location for an input image corresponding to a lowest one of the received frequencies; $\alpha_{high}$ corresponds to a depth dependent a value of the highest one of the received frequencies; and $\alpha_{mid}$ corresponds to a depth dependent a value of the middle one of the received frequencies.

Example 10 includes the subject matter of Example 8, wherein for said each pixel location, an output irradiance at the output image is given by: $I_{out}(r,\theta)=I_{high} \cdot \alpha_{high}(r,\theta)+(1-\alpha_{high}(r,\theta)) \cdot (\alpha_{mid}(r,\theta) \cdot I_{mid}+(1-\alpha_{mid}(r,\theta)) \cdot I_{low})$ where: r: depth; $\theta$: angle; $I_{out}(r,\theta)$: output pixel irradiance at depth r and at image angle $\theta$; $I_{high}$: pixel irradiance at depth r and at image angle $\theta$ for a highest one of the received frequencies; $I_{mid}$: pixel irradiance at depth r and at image angle $\theta$ for a middle one of the received frequencies; $I_{low}$: pixel irradiance at depth r and at image angle $\theta$ for a lowest one of the received frequencies; $\alpha_{high}$ corresponds to an alpha value of the highest one of the received frequencies at depth r and image angle $\theta$; and $\alpha_{mid}$ corresponds to an alpha value at the middle one of the received frequencies at depth r and image angle $\theta$.

Example 11 includes the subject matter of Example 5, wherein maximum and minimum adaptive compounding includes, for each pixel location, using a blend of maximum, minimum and mean pixel irradiances as between the N input images.

Example 12 includes the subject matter of Example 11, wherein for said each pixel location, an output irradiance at the output image is given by: $I_{out}=I_{max} \cdot \alpha_{max}+(1-\alpha_{max}) \cdot (\alpha_{min} \cdot I_{min}+(1-\alpha_{min}) \cdot I_{depth\_comp})$ where: $I_{max}$: MAX $(I_{high}, I_{mid}, I_{low})$; $I_{min}$: MIN $(I_{high}, I_{mid}, I_{low})$; $I_{depth\_comp}$ corresponds to pixel irradiance at the pixel location after alpha blending with depth compensation; $\alpha_{max}$ corresponds to a maximum transparency alpha value coefficient based on at least one of $I_{max}$, $I_{min}$, or $I_{depth\_comp}$, $\alpha_{max}$ having a set first value between and including 0 and 1; and $\alpha_{min}$ corresponds to a minimum transparency alpha value coefficient based on at least one of $I_{max}$, $I_{min}$, or $I_{depth\_comp}$, $\alpha_{min}$ having a set second value different from the set first value and between and including 0 and 1.

Example 13 includes the subject matter of Example 5, wherein predictive compounding includes: determining a relationship between first electrical signals corresponding to a first region at a first input image corresponding to a first reflected frequency, and second electrical signals corresponding to the first region at a second input image corresponding to a second reflected frequency; and predicting, based on the relationship, third electrical signals corresponding to a second region of the second input image.

Example 14 includes the subject matter of Example 13, wherein pixel irradiance of a pixel at the second region is given by: $I_{FF2}=I_{FF1} \cdot I_{NF2}/I_{NF1}$ where: FF1 is the second region in the first input image; FF2 is the second region in the second input image; NF1 is the first region in the first input image; NF2 is the first region in the second input image; $I_{FF2}$ is pixel irradiance at FF2; $I_{FF1}$ is pixel irradiance at region FF1; $I_{NF2}$ is pixel irradiance at region NF2; and $I_{NF1}$ is pixel irradiance at region NFL.

Example 15 includes the subject matter of Example 13, wherein pixel irradiance of a pixel at the second region is given by: $I_{FF2}=I_{NF2} \times (I_{FF1}*PSF2_{inverse})/(I_{NF1}*PSF1_{inverse})$ where: FF1 is the second region in the first input image; FF2 is the second region in the second input image; NF2 is the first region in the second input image; $I_{FF2}$ is pixel irradiance at FF2; $I_{FF1}$ is pixel irradiance at region FF1; $I_{NF2}$ is pixel irradiance at region NF2; PSF1 corresponds to point spread function (PSF) for the first received frequency; PSF2 corresponds to PSF for a second received frequency; $PSF1_{inverse}$ is an inverse of PSF1 corresponding to a deconvolution; and $PSF1_{inverse}$ is an inverse of PSF1 corresponding to a deconvolution.

Example 16 includes the subject matter of Example 13, wherein ML-based compounding includes: determining the first region to correspond to a near field region; determining the second region to correspond to a far field region; segmenting the near field region into a plurality of subregions, for example square subregions; generating a training data set based on multiple first input images and multiple first output images at the near field region; developing a ML-based model for a relationship between pixel irradiances at the first reflected frequency at the first region and pixel irradiances at the second reflected frequency at the first region based on the training data set; and predicting pixel irradiances at the second reflected frequency at the second region based on the model.

Example 17 includes the subject matter of Example 16, wherein ML-based compounding further includes generating a validation data set based on multiple first input images and multiple first output images at a midfield region of the input images, and developing the ML-based model based on the training data set and the validation data set.

Example 18 includes the subject matter of Example 5, wherein color Doppler compounding includes combining, for each pixel location, respective pixel irradiances as between the N input images based on at least one of depth, angle, signal-to-noise ratio, information regarding flow velocity or power.

Example 19 includes the subject matter of Example 18, wherein a $R0_{out}$ and $R1_{out}$ of the output image is given by: $R0_{out}=\alpha \cdot R0_{out.max}+(1-\alpha) \cdot R0_{out.mean}$ and $R1_{out}=\alpha \cdot R1_{out.max}+(1-\alpha) \cdot R1_{out.mean}$ where: $R0_{out}$: zero lag output corresponding to an alpha blended value of max and mean zero lag autocorrelations; $R1_{low}$: first lag output corresponding to an alpha blended value of the max and mean first lag autocorrelations; a: alpha value for the alpha blending; $R0_{out.max}$: the maximum zero lag output value of the autocorrelation corresponding to the alpha-blending to be used; $R1_{out.max}$: the maximum first lag output value of the autocorrelation; $R0_{out.mean}$: the mean zero lag output value of the autocorrelation corresponding to the alpha-blending to be used; $R1_{out.mean}$: the mean first lag output value of the autocorrelation; $R0_{in}(i)$: the zero lag input value corresponding to the frequency band of imaging waveforms for the autocorrelation corresponding to the alpha-blending to be used; and $R1_{in}(i)$: the first lag input value corresponding to the frequency band of imaging waveforms for the autocorrelation corresponding to the alpha-blending to be used.

Example 20 includes the subject matter of any one of Examples 1-4, wherein the respective reflected frequencies include 1.75 MHz, 3.5 MHz and 5.0 MHz, and one of: a fundamental frequency of the transmitted ultrasonic waveform is a single frequency of 1.75 MHz; or respective fundamental frequencies of the transmitted ultrasonic waveform include 1.75 MHz, 3.5 MHz and 5.0 MHz.

Example 21 includes a system including: a user interface device including a display device; and a computing device communicatively coupled to the user interface device, the computing device comprising a memory, and one or more processors coupled to the memory to: receive, simultaneously, electrical signals based on respective reflected frequencies of a reflected ultrasonic waveform reflected from a target object as a result of a transmitted ultrasonic waveform; compound information from the electrical signals to generate compounded electrical signals; and cause generation of an output image on a display device based on the compounded electrical signals.

Example 22 includes the subject matter of Example 21, wherein the respective reflected frequencies correspond to respective harmonics of a fundamental frequency of the transmitted ultrasonic waveform, the fundamental frequency being a single frequency of the transmitted ultrasonic waveform.

Example 23 includes the subject matter of Example 21, wherein the transmitted ultrasonic waveform is a multimodal waveform with fundamental frequencies that correspond to the respective frequencies of the reflected ultrasonic waveform.

Example 24 includes the subject matter of Example 21, wherein the one or more processors are to compound the information by: implementing a predictive algorithm on the electrical signals, the one or more processors to use information from first electrical signals corresponding to a first image region of the target object to generate predictive electrical signals for a second image region of the target object different from the first image region; and using the predictive electrical signals to obtain the compounded electrical signals such that the output image at the second image region corresponds to the predictive electrical signals.

Example 25 includes the subject matter of any one of Examples 21-24, wherein: the reflected frequencies include N reflected frequencies; the electrical signals include N sets of electrical signals, with each set of electrical signals corresponds to one of the reflected frequencies, the N sets of electrical signals corresponding to N input images of the target object; individual input images include pixels at respective pixel locations, with each pixel location of the N input images being defined by a depth and an angle; compounding information includes compounding information from the N sets of electrical signals; and the one or more processors are to compound the information from the N sets of electrical signals by using at least one of simple averaging, weighted averaging, alpha blending with depth adaptive compounding, maximum and minimum adaptive compounding, predictive compounding, lateral frequency compounding and color Doppler compounding.

Example 26 includes the subject matter of Example 25, where the one or more processors are further to subject the electrical signals to gain compensation or dynamic range compensation prior to compounding.

Example 27 includes the subject matter of Example 25, wherein simple averaging includes, for each pixel location, performing one of a simple averaging or a weighted averaging of respective pixel irradiances across the N input images.

Example 28 includes the subject matter of Example 25, wherein alpha blending with depth adaptive compounding includes, for each pixel location, multiplying, by a corresponding alpha multiplier, respective pixel irradiances as between the N input images, each alpha multiplier a function of one or more alpha values, the one or more alpha values a function of at least one of depth of said each pixel location or angle of said each pixel location.

Example 29 includes the subject matter of Example 28, wherein, for said each pixel location, an output irradiance at the output image is given by: $I_{out}=I_{high} \cdot \alpha_{high}+(1-\alpha_{high}) \cdot (\alpha_{mid} \cdot I_{mid}+(1-\alpha_{mid}) \cdot I_{low})$ where: $I_{out}$ is an output pixel irradiance for said each pixel location for the output image; $I_{high}$ is a pixel irradiance for said each pixel location for an input image corresponding to a highest one of the received frequencies; $I_{mid}$ is a pixel irradiance for said each pixel location for an input image corresponding to a middle one of the received frequencies; $I_{low}$ is a pixel irradiance for said each pixel location for an input image corresponding to a lowest one of the received frequencies; $\alpha_{high}$ corresponds to a depth dependent a value of the highest one of the received frequencies; and $\alpha_{mid}$ corresponds to a depth dependent a value of the middle one of the received frequencies.

Example 30 includes the subject matter of Example 28, wherein for said each pixel location, an output irradiance at the output image is given by: $I_{out}(r,\theta)=I_{high} \cdot \alpha_{high}(r,\theta)+(1-\alpha_{high}(r,\theta)) \cdot (\alpha_{mid}(r,\theta) \cdot I_{mid}+(1-\alpha_{mid}(r,\theta)) \cdot I_{low})$ where: r: depth; θ: angle; $I_{out}(r,\theta)$: output pixel irradiance at depth r and at image angle θ; $I_{high}$: pixel irradiance at depth r and at image angle θ for a highest one of the received frequencies; $I_{mid}$: pixel irradiance at depth r and at image angle θ for a middle one of the received frequencies; $I_{low}$: pixel irradiance at depth r and at image angle θ for a lowest one of the received frequencies; $\alpha_{high}$: an alpha value of the highest one of the received frequencies at depth r and image angle θ; and $\alpha_{mid}$: an alpha value at the middle one of the received frequencies at depth r and image angle θ.

Example 31 includes the subject matter of Example 25, wherein maximum and minimum adaptive compounding includes, for each pixel location, using a blend of maximum, minimum and mean pixel irradiances as between the N input images.

Example 32 includes the subject matter of Example 31, wherein for said each pixel location, an output irradiance at the output image is given by: $I_{out}=I_{max} \cdot \alpha_{max}+(1-\alpha_{max}) \cdot (\alpha_{min} \cdot I_{min}+(1-\alpha_{min}) \cdot I_{depth\_comp})$ where: $I_{max}$: MAX ($I_{high}$, $I_{mid}$, $I_{low}$), $I_{min}$: MIN ($I_{high}$, $I_{mid}$, $I_{low}$); $I_{depth\_comp}$ corresponds to pixel irradiance at the pixel location after alpha blending with depth compensation; $\alpha_{max}$ corresponds to a maximum transparency alpha value coefficient based on at least one of $I_{max}$, $I_{min}$, or $I_{depth\_comp}$, $\alpha_{max}$ having a set first value between and including 0 and 1; and $\alpha_{min}$ corresponds to a minimum transparency alpha value coefficient based on at least one of $I_{max}$, $I_{min}$, or $I_{depth\_comp}$, $\alpha_{min}$ having a set second value different from the set first value and between and including 0 and 1.

Example 33 includes the subject matter of Example 25, wherein predictive compounding includes: determining a relationship between first electrical signals corresponding to a first region at a first input image corresponding to a first reflected frequency, and second electrical signals corresponding to the first region at a second input image corresponding to a second reflected frequency; and predicting, based on the relationship, third electrical signals corresponding to a second region of the second input image.

Example 34 includes the subject matter of Example 33, wherein pixel irradiance of a pixel at the second region is given by: $I_{FF2}=I_{FF1} \cdot I_{NF2}/I_{NF1}$ where: FF1 is the second region in the first input image; FF2 is the second region in the second input image; NF1 is the first region in the first input image; NF2 is the first region in the second input image; $I_{FF2}$ is pixel irradiance at FF2; $I_{FF1}$ is pixel irradiance at region FF1; $I_{NF2}$ is pixel irradiance at region NF2; and $I_{NF1}$ is pixel irradiance at region NFL.

Example 35 includes the subject matter of Example 33, wherein pixel irradiance of a pixel at the second region is given by: $I_{FF2}=I_{NF2} \times (I_{FF1}*PSF2_{inverse})/(I_{NF1}*PSF1_{inverse})$ where: FF1 is the second region in the first input image; FF2 is the second region in the second input image; NF2 is the first region in the second input image; $I_{FF2}$ is pixel irradiance at FF2; $I_{FF1}$ is pixel irradiance at region FF1; $I_{NF2}$ is pixel irradiance at region NF2; PSF1 corresponds to point spread function (PSF) for a first received frequency; PSF2 corresponds to PSF for a second received frequency; $PSF1_{inverse}$ is an inverse of PSF1 corresponding to a deconvolution; and $PSF1_{inverse}$ is an inverse of PSF1 corresponding to a deconvolution.

Example 36 includes the subject matter of Example 33, wherein ML-based compounding includes: determining the first region to correspond to a near field region; determining the second region to correspond to a far field region; segmenting the near field region into a plurality of subregions, for example square subregions; generating a training data set based on multiple first input images and multiple first output images at the near field region; developing a ML-based model for a relationship between pixel irradiances at the first reflected frequency at the first region and pixel irradiances at the second reflected frequency at the first region based on the training data set; and predicting pixel irradiances at the second reflected frequency at the second region based on the model.

Example 37 includes the subject matter of Example 36, wherein ML-based compounding further includes generating a validation data set based on multiple first input images and multiple first output images at a midfield region of the input images, and developing the ML-based model based on the training data set and the validation data set.

Example 38 includes the subject matter of Example 25, wherein color Doppler compounding includes combining, for each pixel location, respective pixel irradiances as between the N input images based on at least one of depth, angle, signal-to-noise ratio, information regarding flow velocity or power.

Example 39 includes the subject matter of Example 38, wherein a $R0_{out}$ and $R1_{out}$ of the output image is given by: $R0_{out} = \alpha \cdot R0_{out.max} + (1-\alpha) \cdot R0_{out.mean}$ and $R1_{out} = \alpha \cdot R1_{out.max} + (1-\alpha) \cdot R1_{out.mean}$ where: $R0_{out}$: zero lag output corresponding to an alpha blended value of max and mean zero lag autocorrelations; $R1_{out}$: first lag output corresponding to an alpha blended value of the max and mean first lag autocorrelations; a: alpha value for the alpha blending; $R0_{out.max}$: the maximum zero lag output value of the autocorrelation corresponding to the alpha-blending to be used; $R1_{out.max}$: the maximum first lag output value of the autocorrelation; $R0_{out.mean}$: the mean zero lag output value of the autocorrelation corresponding to the alpha-blending to be used; $R1_{out.mean}$: the mean first lag output value of the autocorrelation; $R0_{in}(i)$: the zero lag input value corresponding to the frequency band of imaging waveforms for the autocorrelation corresponding to the alpha-blending to be used; and $R1_{in}(i)$: the first lag input value corresponding to the frequency band of imaging waveforms for the autocorrelation corresponding to the alpha-blending to be used.

Example 40 includes the subject matter of any one of Examples 21-24, wherein the respective reflected frequencies include 1.75 MHz, 3.5 MHz and 5.0 MHz, and one of: a fundamental frequency of the transmitted ultrasonic waveform is a single frequency of 1.75 MHz; or respective fundamental frequencies of the transmitted ultrasonic waveform include 1.75 MHz, 3.5 MHz and 5.0 MHz.

Example 41 includes a method to be performed at a computing device comprising a memory, and one or more processors coupled to the memory, the method including: receiving, simultaneously, electrical signals based on respective reflected frequencies of a reflected ultrasonic waveform reflected from a target object as a result of a transmitted ultrasonic waveform; compounding information from the electrical signals to generate compounded electrical signals; and causing generation of an output image on a display device based on the compounded electrical signals.

Example 42 includes the subject matter of Example 41, wherein the respective reflected frequencies correspond to respective harmonics of a fundamental frequency of the transmitted ultrasonic waveform, the fundamental frequency being a single frequency of the transmitted ultrasonic waveform.

Example 43 includes the subject matter of Example 41, wherein the transmitted ultrasonic waveform is a multi-modal waveform with fundamental frequencies that correspond to the respective frequencies of the reflected ultrasonic waveform.

Example 44 includes the subject matter of Example 41, wherein compounding the information includes: implementing a predictive algorithm on the electrical signals, the one or more processors to use information from first electrical signals corresponding to a first image region of the target object to generate predictive electrical signals for a second image region of the target object different from the first image region; and using the predictive electrical signals to obtain the compounded electrical signals such that the output image at the second image region corresponds to the predictive electrical signals.

Example 45 includes the subject matter of Example 41, wherein: the reflected frequencies include N reflected frequencies; the electrical signals include N sets of electrical signals, with each set of electrical signals corresponds to one of the reflected frequencies, the N sets of electrical signals corresponding to N input images of the target object; individual input images include pixels at respective pixel locations, with each pixel location of the N input images being defined by a depth and an angle; compounding information includes compounding information from the N sets of electrical signals; and the method further includes compounding the information from the N sets of electrical signals by using at least one of simple averaging, weighted averaging, alpha blending with depth adaptive compounding, maximum and minimum adaptive compounding, predictive compounding, lateral frequency compounding and color Doppler compounding.

Example 46 includes the subject matter of Example 45, further including subjecting the electrical signals to gain compensation or dynamic range compensation prior to compounding.

Example 47 includes the subject matter of Example 45, wherein simple averaging includes, for each pixel location, performing one of a simple averaging or a weighted averaging of respective pixel irradiances across the N input images.

Example 48 includes the subject matter of Example 45, wherein alpha blending with depth adaptive compounding includes, for each pixel location, multiplying, by a corresponding alpha multiplier, respective pixel irradiances as between the N input images, each alpha multiplier a function of one or more alpha values, the one or more alpha values a function of at least one of depth of said each pixel location or angle of said each pixel location.

Example 49 includes the subject matter of Example 48, wherein, for said each pixel location, an output irradiance at the output image is given by: $I_{out} = I_{high} \cdot \alpha_{high} + (1-\alpha_{high}) \cdot (\alpha_{mid} \cdot I_{mid} + (1-\alpha_{mid}) \cdot I_{low})$ where: $I_{out}$ is an output pixel irradiance for said each pixel location for the output image; $I_{high}$ is a pixel irradiance for said each pixel location for an input image corresponding to a highest one of the received frequencies; $I_{mid}$ is a pixel irradiance for said each pixel location for an input image corresponding to a middle one of the received frequencies; $I_{low}$ is a pixel irradiance for said each pixel location for an input image corresponding to a lowest one of the received frequencies; $\alpha_{high}$ corresponds to a depth dependent a value of the highest one of the received frequencies; and $\alpha_{mid}$ corresponds to a depth dependent a value of the middle one of the received frequencies.

Example 50 includes the subject matter of Example 48, wherein for said each pixel location, an output irradiance at the output image is given by: $I_{out}(r,\theta) = I_{high} \, \alpha_{high}(r,\theta) + (1-\alpha_{high}(r,\theta)) \cdot (\alpha_{mid}(r,\theta) \cdot I_{mid} + (1-\alpha_{mid}(r,\theta)) \cdot I_{low})$ where: r denotes depth; θ denotes angle; $I_{out}(r,\theta)$ is an output pixel irradiance at depth r and at image angle θ; $I_{high}$ is a pixel irradiance at depth r and at image angle θ for a highest one of the received frequencies; $I_{mid}$ is a pixel irradiance at depth r and at image angle θ for a middle one of the received frequencies; $I_{low}$ is a pixel irradiance at depth r and at image angle θ for a lowest one of the received frequencies; $\alpha_{high}$ corresponds to an alpha value of the highest one of the received frequencies at depth r and image angle θ; and $\alpha_{mid}$ corresponds to an alpha value at the middle one of the received frequencies at depth r and image angle θ.

Example 51 includes the subject matter of Example 45, wherein maximum and minimum adaptive compounding includes, for each pixel location, using a blend of maximum, minimum and mean pixel irradiances as between the N input images.

Example 52 includes the subject matter of Example 51, wherein for said each pixel location, an output irradiance at the output image is given by: $I_{out}=I_{max}\ \alpha_{max}+(1-\alpha_{max})\cdot(\alpha_{min}\cdot I_{min}+(1-\alpha_{min})\cdot I_{depth\_comp})$ where: $I_{max}$: MAX ($I_{high}$, $I_{mid}$, $I_{low}$); $I_{min}$: MIN ($I_{high}$, $I_{mid}$, $I_{low}$); $I_{depth\_comp}$ corresponds to pixel irradiance at the pixel location after alpha blending with depth compensation; $\alpha_{max}$ corresponds to a maximum transparency alpha value coefficient based on at least one of $I_{max}$, $I_{min}$, or $I_{depth\_comp}$, $\alpha_{max}$ having a set first value between and including 0 and 1; and $\alpha_{min}$ corresponds to a minimum transparency alpha value coefficient based on at least one of $I_{max}$, $I_{min}$, or $I_{depth\_comp}$, $\alpha_{min}$ having a set second value different from the set first value and between and including 0 and 1.

Example 53 includes the subject matter of Example 45, wherein predictive compounding includes: determining a relationship between first electrical signals corresponding to a first region at a first input image corresponding to a first reflected frequency, and second electrical signals corresponding to the first region at a second input image corresponding to a second reflected frequency; and predicting, based on the relationship, third electrical signals corresponding to a second region of the second input image.

Example 54 includes the subject matter of Example 43, wherein pixel irradiance of a pixel at the second region is given by: $I_{FF2}\ I_{FF1}\cdot I_{NF2}/I_{NF1}$ where: FF1 is the second region in the first input image; FF2 is the second region in the second input image; NF1 is the first region in the first input image; NF2 is the first region in the second input image; $I_{FF2}$ is pixel irradiance at FF2; $I_{FF1}$ is pixel irradiance at region FF1; $I_{NF2}$ is pixel irradiance at region NF2; and $I_{NF1}$ is pixel irradiance at region NF1.

Example 55 includes the subject matter of Example 53, wherein pixel irradiance of a pixel at the second region is given by: $I_{FF2}=I_{NF2}\times(I_{FF1}*PSF2_{inverse})/(I_{NF1}*PSF1_{inverse})$ where: FF1 is the second region in the first input image; FF2 is the second region in the second input image; NF2 is the first region in the second input image; $I_{FF2}$ is pixel irradiance at FF2; $I_{FF1}$ is pixel irradiance at region FF1; $I_{NF2}$ is pixel irradiance at region NF2; PSF1 corresponds to point spread function (PSF) for a first received frequency; PSF2 corresponds to PSF for a second received frequency; $PSF1_{inverse}$ is an inverse of PSF1 corresponding to a deconvolution; and $PSF1_{inverse}$ is an inverse of PSF1 corresponding to a deconvolution.

Example 56 includes the subject matter of Example 53, wherein ML-based compounding includes: determining the first region to correspond to a near field region; determining the second region to correspond to a far field region; segmenting the near field region into a plurality of subregions, for example square subregions; generating a training data set based on multiple first input images and multiple first output images at the near field region; developing a ML-based model for a relationship between pixel irradiances at the first reflected frequency at the first region and pixel irradiances at the second reflected frequency at the first region based on the training data set; and predicting pixel irradiances at the second reflected frequency at the second region based on the model.

Example 57 includes the subject matter of Example 56, wherein ML-based compounding further includes generating a validation data set based on multiple first input images and multiple first output images at a midfield region of the input images, and developing the ML-based model based on the training data set and the validation data set.

Example 58 includes the subject matter of Example 45, wherein color Doppler compounding includes combining, for each pixel location, respective pixel irradiances as between the N input images based on at least one of depth, angle, signal-to-noise ratio, information regarding flow velocity or power.

Example 59 includes the subject matter of Example 58, wherein a $R0_{out}$ and $R1_{out}$ of the output image is given by: $R0_{out}=\alpha\cdot R0_{out.max}+(1-\alpha)\cdot R0_{out.mean}$ and $R1_{out}=\alpha\cdot R1_{out.max}+(1-\alpha)\cdot R1_{out.mean}$ where: $R0_{out}$: zero lag output corresponding to an alpha blended value of max and mean zero lag autocorrelations; $R1_{low}$: first lag output corresponding to an alpha blended value of the max and mean first lag autocorrelations; a: alpha value for the alpha blending; $R0_{out.max}$: the maximum zero lag output value of the autocorrelation corresponding to the alpha-blending to be used; $R1_{out.max}$: the maximum first lag output value of the autocorrelation; $R0_{out.mean}$: the mean zero lag output value of the autocorrelation corresponding to the alpha-blending to be used; $R1_{out.mean}$: the mean first lag output value of the autocorrelation; $R0_{in}(i)$: the zero lag input value corresponding to the frequency band of imaging waveforms for the autocorrelation corresponding to the alpha-blending to be used; and $R1_{in}(i)$: the first lag input value corresponding to the frequency band of imaging waveforms for the autocorrelation corresponding to the alpha-blending to be used.

Example 60 includes the subject matter of Example 41, wherein the respective reflected frequencies include 1.75 MHz, 3.5 MHz and 5.0 MHz, and one of: a fundamental frequency of the transmitted ultrasonic waveform is a single frequency of 1.75 MHz; or respective fundamental frequencies of the transmitted ultrasonic waveform include 1.75 MHz, 3.5 MHz and 5.0 MHz.

Example 61 includes an apparatus comprising means for performing the method of any one of claims 41-60.

Example 62 includes one or more computer-readable media comprising a plurality of instructions stored thereon that, when executed, cause one or more processors to perform the method of any one of claims 41-60.

Example 63 includes an imaging device comprising the apparatus of any one of claims 1-20, and further including the user interface device.

Example 64 includes a product comprising one or more tangible computer-readable non-transitory storage media comprising computer-executable instructions operable to, when executed by at least one computer processor, enable the at least one processor to perform the method of any one of Examples 21-40.

What is claimed is:

1. An apparatus of a computing device comprising a memory, and one or more processors coupled to the memory to:
   receive, simultaneously, electrical signals based on respective reflected frequencies of a reflected ultrasonic waveform reflected from a target object as a result of a transmitted ultrasonic waveform, the reflected frequencies including N reflected frequencies, and the electrical signals including N sets of electrical signals, with each set of electrical signals corresponding to one of the reflected frequencies, the N sets of electrical signals corresponding respectively to N input images of the target object, individual input images including pixels at respective pixel locations;

compound information from the electrical signals to generate compounded electrical signals, wherein compounding includes:
  determining a relationship between, on one hand, a first set of electrical signals corresponding to a first image region of the target object at a first one of the reflected frequencies, and, on another hand, a first set of electrical signals corresponding to the first image region of the target object at a second one of the reflected frequencies; and
  using the relationship to predict a second set of electrical signals corresponding to a second image region of the target object at the second one of the reflected frequencies based on a second set of electrical signals corresponding to the second image region of the target object at the first one of the reflected frequencies; and
cause generation of an output image on a display based on the compounded electrical signals.

2. The apparatus of claim 1, wherein the respective reflected frequencies correspond to respective harmonics of a fundamental frequency of the transmitted ultrasonic waveform, the fundamental frequency being a single frequency of the transmitted ultrasonic waveform.

3. The apparatus of claim 1, wherein the transmitted ultrasonic waveform is a multimodal waveform with fundamental frequencies that correspond to the respective frequencies of the reflected ultrasonic waveform.

4. A system including:
a user interface device including a display device; and
a computing device communicatively coupled to the user interface device, the computing device comprising a memory, and one or more processors coupled to the memory to:
  receive, simultaneously, electrical signals based on respective reflected frequencies of a reflected ultrasonic waveform reflected from a target object as a result of a transmitted ultrasonic waveform, the reflected frequencies including N reflected frequencies, and the electrical signals including N sets of electrical signals, with each set of electrical signals corresponding to one of the reflected frequencies, the N sets of electrical signals corresponding respectively to N input images of the target object, individual input images including pixels at respective pixel locations;
  compound information from the electrical signals to generate compounded electrical signals, wherein compounding includes:
    determining a relationship between, on one hand, a first set of electrical signals corresponding to a first image region of the target object at a first one of the reflected frequencies, and, on another hand, a first set of electrical signals corresponding to the first image region of the target object at a second one of the reflected frequencies; and
    using the relationship to predict a second set of electrical signals corresponding to a second image region of the target object at the second one of the reflected frequencies based on a second set of electrical signals corresponding to the second image region of the target object at the first one of the reflected frequencies; and
  cause generation of an output image on a display device based on the compounded electrical signals.

5. A tangible non-transitory machine-readable storage medium having instructions stored thereon, the instructions when executed by one or more processors of a computing device to cause the one or more processors to perform operations including:
receiving, simultaneously, electrical signals based on respective reflected frequencies of a reflected ultrasonic waveform reflected from a target object as a result of a transmitted ultrasonic waveform, the reflected frequencies including N reflected frequencies, and the electrical signals including N sets of electrical signals, with each set of electrical signals corresponding to one of the reflected frequencies, the N sets of electrical signals corresponding respectively to N input images of the target object, individual input images including pixels at respective pixel locations;
compounding information from the electrical signals to generate compounded electrical signals, wherein compounding includes:
  determining a relationship between, on one hand, a first set of electrical signals corresponding to a first image region of the target object at a first one of the reflected frequencies, and, on another hand, a first set of electrical signals corresponding to the first image region of the target object at a second one of the reflected frequencies; and
using the relationship to predict a second set of electrical signals corresponding to a second image region of the target object at the second one of the reflected frequencies based on a second set of electrical signals corresponding to the second image region of the target object at the first one of the reflected frequencies; and
causing generation of an output image on a display device based on the compounded electrical signals.

* * * * *